(12) United States Patent
Mollick et al.

(10) Patent No.: US 9,587,032 B2
(45) Date of Patent: Mar. 7, 2017

(54) IGE ANTIBODIES FOR THE INHIBITION OF TUMOR METASTASIS

(71) Applicant: The Board of Trustees of the Leland Stanford Junior University, Palo Alto, CA (US)

(72) Inventors: Joseph A. Mollick, Palo Alto, CA (US); Pearline Teo, Buona Vista (SG); Paul J. Utz, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 37 days.

(21) Appl. No.: 13/939,781

(22) Filed: Jul. 11, 2013

(65) Prior Publication Data

US 2014/0370001 A1    Dec. 18, 2014

Related U.S. Application Data

(60) Provisional application No. 61/834,169, filed on Jun. 12, 2013.

(51) Int. Cl.
*C07K 16/28* (2006.01)
*C07K 16/30* (2006.01)
*A61K 39/00* (2006.01)

(52) U.S. Cl.
CPC ...... *C07K 16/2887* (2013.01); *C07K 16/3092* (2013.01); *A61K 2039/505* (2013.01); *C07K 2317/52* (2013.01); *C07K 2317/70* (2013.01); *C07K 2317/73* (2013.01)

(58) Field of Classification Search
CPC ..... A61K 2039/505; G01N 2800/7028; G01N 2800/00; C07K 16/00; C07K 16/32; C07K 16/30
See application file for complete search history.

(56) References Cited

U.S. PATENT DOCUMENTS

| | | | |
|---|---|---|---|
| 2005/0118651 A1 | 6/2005 | Basi et al. | |
| 2006/0292643 A1 | 12/2006 | Goletz et al. | |
| 2009/0136520 A1* | 5/2009 | Kufe | 424/172.1 |
| 2010/0098683 A1* | 4/2010 | Kufe | 424/130.1 |
| 2010/0105873 A1* | 4/2010 | Allan et al. | 530/387.1 |
| 2011/0021755 A1* | 1/2011 | Lazar et al. | 530/387.1 |
| 2012/0040375 A1* | 2/2012 | Nishimura et al. | 435/7.23 |
| 2012/0258119 A1 | 10/2012 | Renner et al. | |
| 2013/0022614 A1 | 1/2013 | Penichet et al. | |
| 2013/0034557 A1 | 2/2013 | Nishimura et al. | |

FOREIGN PATENT DOCUMENTS

WO    2013/028231 A1    2/2013

OTHER PUBLICATIONS

Stancovski et al. (PNAS, 88: 8691-8695, 1991).*
Jiang et al. (J. Biol. Chem., 280: 4656-4662, 2005).*
Teo, P. Z., et al., "Using the allergic immune system to target cancer: activity of IgE antibodies specific for human CD20 and MUC1," Cancer Immunol. Immunother. (2012).
Toh, B., et al., "Myeloid cells Prime drivers of tumor progression," OncoImmunology, 1(8): 1360-1367; Nov. 2012.
Daniels, T. R., et al., "Targeting HER2/neu with a fully human IgE to harness the allergic reaction against cancer cells," Cancer Immunol. Immunother. (2011).
Daniels, T. R., et al., "Animal models for IgE-meditated cancer immunotherapy," Cancer Immunol. Immunother. (2011).
Karagiannis, P. et al., "Characterisation of an engineered trastuzumab IgE antibody and effector cell mechanisms targeting HER2/neu-positive tumour cells," Cancer Immunol. Immunother., 58: 915-930 (2009).
Muthuswamy, R., et al., "NF-κB hyperactivation in tumor tissues allows tumor-selective reprogramming of chemokine microenvironment to enhance the recruitment of cytolytic T effector cells," Cancer Res. in Press (2012).
Dalton, D. K., et al., "The roles of mast cells in anticancer immunity," Cancer Immunol. Immunother. (2012).
Coussens, L. M., et al., "Neutralizing Tumor-Promoting Chronic Inflammation: A Magic Bullet?" Science, 339: 286-291 (2013).
Rudman, S. M., et al., "Harnessing engineered antibodies of the IgE class to combat malignancy: initial assessment of FcεRI-mediated basophil activation by a tumourspecific IgE antibody to evaluate the risk of type I hypersensitivity," Clinical & Experimental Allergy, 41, 1400-1413 (2011).
Spillner, E., et al., "Recombinant IgE antibody engineering to target EGFR," Cancer Immunol. Immunother., 61: 1565-1573 (2012).
Karagiannis, S. N., et al., "Role of IgE receptors in IgE antibody-dependent cytotoxicity and phagocytosis of ovarian tumor cells by human monocytic cells," Cancer Immunol. Immunother., 57: 247-263 (2008).
Extended European Search Report No. EP 14811351.7, May 9, 2016.
Daniels et al.; "The IgE Antibody and Its Use in Cancer Immunotherapy", Humana Press, XP008179200, Cancer and IgE, Introducing the Concept of AllergoOncology, Chapter 7, Springer Science+Business Media, LLC 2010, p. 159-183.
Danussi et al.: "A newly generated functional antibody identifies Tn antigen as a novel determinant in the cancer cell-lymphatic endothelium interaction", Glycobiology, vol. 19, No. 10, pp. 1056-1067, 2009.
Homayounfar et al.; "Multimodal treatment options for bilobar colorectal liver metastases", Langenbecks Arch. Surg. (2010) 395:633-641.
Karagiannis et al.; "IgE Interacts with Potent Effector Cells Against Tumors: ADCC and ADCP", Humana Press, Cancer and IgE, Introducing the Concepts of AllergoOncology, Chapter 8, Springer Science+Business Media, LLC 2010, pp. 185-213.

* cited by examiner

Primary Examiner — Brad Duffy
Assistant Examiner — Nelson B Moseley, II
(74) Attorney, Agent, or Firm — Kilpatrick Townsend & Stockton LLP

(57) ABSTRACT

The present invention provides novel IgE antibodies useful for inhibiting or preventing metastatic cancer. Also provided are methods to inhibit tumor metastasis by modulating the activity of at least one non-tumor cell, treating a patient to inhibit or prevent tumor metastases of a primary solid tumor, treating metastatic carcinoma, reducing metastasis of carcinoma cells, and reducing the growth kinetics of a primary solid tumor or a metastasized cell or tumor.

13 Claims, 7 Drawing Sheets

SEQUENCE LISTING

```
<160> NUMBER OF SEQ ID NOS: 5

<210> SEQ ID NO 1
<211> LENGTH: 428
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3C6.hIgE heavy chain variable

<400> SEQUENCE: 1
gccgccacca tgtacttggg actgaactgt gtattcatag tttttctctt aaatggtgtc      60
cagagtgaag tgaagcttga ggagtctgga ggaggcttgg tgcaacctgg aggatccatg     120
aaactctctt gtgctgcctc tggattcact tttagtgacg cctggatgga ctgggtccgc     180
cagtctccag agaaggggct tgagtgggtt gctgaaatta agcaaagc taataatcat     240 gcaacatact atgctgagtc tgtgaaaggg aggttcacca tctcaagaga tgtttccaaa     300
agtagtgtct acctgcaaat gaacaactta agagctgaag acactggcat ttattactgt     360 accaggggg ggtacggctt tgactactgg ggccaaggca ccactctcac agtctcctca     420
ggtaagtg                                                              428

<210> SEQ ID NO 2
<211> LENGTH: 409
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<223> OTHER INFORMATION: 3C6.hIgE light chain variable

<400> SEQUENCE: 2
gccgccacca tgaagttgcc tgttaggctg ttggtgctga tgttctggat tcctgcttcc      60
agcagtgatg ttttgatgac ccaaactcca ctctccctgc ctgtcagtct tggagatcaa     120
gcctccatct cttgcagatc tagtcagagc attgtacata gtaatggaaa cacctattta     180
gaatggtacc tgcagaaacc aggccagtct ccaaagctcc tgatctacaa agtttccaac     240
cgattttctg ggtcccaga caggttcagt ggcagtggat cagggacaga tttcacactc      300
aagatcagca gtggaggc tgaggatctg gagtttatt actgctttca aggttcacat       360
gttccgctca cgttcggtgc tgggaccaag ctggagctga acgtaagt                  409

<210> SEQ ID NO 3
<211> LENGTH: 427
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 4H5.hIgE monoclonal antibody heavy chain
      variable region

<400> SEQUENCE: 3
gccgccacca tgggatggag ctgtatcatg ctcttttgg tagcaacagc aacaggtgtc      60
cactcccagg tccaactgca gcagtctggg gctgaactgg tgaagcctgg ggcttcagtg    120
aagttgtcct gcaaggcttc tggctacacc ttcaccagct actatatgta ctgggtgaag    180
cagaggcctg gacaaggcct tgagtggatt ggagagatta atcctagcaa tggtggtact    240
gacttcaatg agaagttcaa gagcaaggcc acactgactg tagacaaatc ctccagcaca    300
gcatacatgc aactcagcag cctgacatct gcggactctg cggtctatta ctgtacaagg    360
gggggtgatt acccctggtt tgcttactgg ggccaaggga ctctggtcac tgtctctgca    420
ggtaagt                                                              427

<210> SEQ ID NO 4
<211> LENGTH: 415
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 4H5.hIgE monoclonal antibody heavy chain
      variable region

<400> SEQUENCE: 4
gccgccacca tggattcaca ggcccaggtt cttatgttac tgctgctatg ggtatctggt      60
acctgtgggg acattgtgat gtcacagtct ccatcctccc tagctgtgtc agttggagag    120
aaggttacta tgagctgcaa gtccagtcag agccttttat atagtagcaa tcaaaagaac    180
tacttggcct ggtaccagca gaaaccaggg cagtctccta aactgctgat ttactgggca    240
tccactaggg aatctggggt ccctgatcgc ttcacaggca gtggatctgg gacagatttc    300
actctcacca tcagcagtgt gaaggctgaa gacctggcag tttattactg tcagcaatat    360
tatagctatc ctctcacgtt cggtgctggg accaagctgg agctgaaacg taagt         415
```

```
<210> SEQ ID NO 5
<211> LENGTH: 20
<212> TYPE: PRT
<213> ORGANISM: Homo sapiens
<220> FEATURE:
<223> OTHER INFORMATION: Amino Acid Sequence of MUC1 epitope

<400> SEQUENCE: 5

Ser Thr Ala Pro Pro Ala His Gly Val Thr Ser Ala Pro Asp Thr Arg
1               5                   10                  15

Pro Ala Pro Gly
            20
```

IGE ANTIBODIES FOR THE INHIBITION OF TUMOR METASTASIS

RELATED APPLICATION

This application claims the benefit of U.S. Provisional Application No. 61/834,169, filed on Jun. 12, 2013. The entire teachings of the above application are incorporated herein by reference.

SEQUENCE LISTING

The instant application contains a Sequence Listing which has been submitted electronically in ASCII format and is hereby incorporated by reference in its entirety. Said ASCII copy, created on Oct. 30, 2013, is named 4173.3003 US1SeqList.txt and is 3,816 bytes in size.

GOVERNMENT SUPPORT

This invention was made with government support under contract CA111639 awarded by the National Institutes of Health. The government has certain rights in the invention.

BACKGROUND OF THE INVENTION

IgE antibodies mediate allergic and asthmatic reactions, characterized by immediate hypersensitivity and an inflammatory delayed-type responses requiring the recruitment of effector cells. IgE antibodies are transported from the peripheral circulation into tissues, where they can bind allergic effector cells such as mast cells, basophils, eosinophils, dendritic cells, Langerhans cells, monocytes, and macrophages via three types of Fc receptors: FcεRI (or high-affinity FcεR) ($K_a=10^{11}$ $M^{-1}$), FcεRII (or low-affinity FcεR, CD23) ($K_a<10^8$ $M^{-1}$), and galectin-3. Unlike antibodies of the IgG class, IgE binds to its FcR with extremely high affinity, which in the case of FcεRI is about three orders of magnitude higher than that of IgG for the FcRs (FcγRI-III) and in the case of FcεRII is as high as that of IgG for its high affinity FcγRI (Gould, H J, et al., *Annu. Rev. Immunol.,* 21: 579-628. (2003); Gounni, A S, et al., *Nature,* 367: 183-186 (1994); Kinet, J P, *Annu. Rev. Immunol.,* 17: 931-72:931-972 (1999) and Ravetch J V, and Kinet J P, *Annu. Rev. Immunol.,* 9: 457-492 (1991)).

The newly arising field of AllergoOncology is based upon observations and studies suggesting an inverse correlation between IgE-mediated allergy and cancer (Turner M C, et al., *Int. J. Cancer,* 118: 3124-3132 (2006); Wang H & Diepgen T L, *Allergy* 60: 1098-1111, (2005); Turner M C, et al., *Am. J. Epidemiol.,* 162: 212-221 (2005); Wang H, et al., *Int. J. Cancer,* 119: 695-701 (2006); Mills P K, et al., *Am. J. Epidemiol.,* 136: 287-295 (1992); Wiemels J L, et al., *Cancer Res.,* 64: 8468-8473 (2004); Dodig S., et al., *Acta Pharm.,* 55: 123-138 (2005); and Wrensch M., et al., *Cancer Res.,* 66: 4531-4541 (2006)). As a result, researchers in this field are exploring the therapeutic potential of the IgE antibody class in the prevention and treatment of certain cancers, under the premise that immune responses originally developed as adaptive responses to microbial/parasitic infection might be useful when directed against malignancy.

The application of IgE for the therapy of cancer was pioneered by Nagy et al. (Nagy, E., et al., *Cancer Immunol. Immunother.,* 34: 63-69 (1991)), who developed a murine IgE monoclonal antibody specific for the major envelope glycoprotein (gp36) of mouse mammary tumor virus (MMTV) and demonstrated significant anti-tumor activity in C3H/HeJ mice bearing a syngeneic MMTV-secreting mammary adenocarcinoma (H2712) (Nagy, E., et al., *Cancer Immunol. Immunother.,* 34: 63-69 (1991)). Kershaw et al. (Kershaw, M H, et al., *Oncol. Res.,* 10: 133-142 (1998)) developed a murine monoclonal IgE named 30.6, specific for an antigenic determinant expressed on the surface of colorectal adenocarcinoma cells. Mouse IgE 30.6 inhibited the growth of established human colorectal carcinoma COLO 205 cells growing subcutaneously in severe combined immune deficient (SCID) mice, although this effect was transient. By contrast, a mouse IgG 30.6 did not show anti-tumor effects. The mouse IgE specific effect was attributed to the interaction of the antibody with FcεR bearing effector cells since the activity was specifically abrogated by prior administration of a nonspecific mouse IgE (Kershaw, M H, et al., *Oncol. Res.,* 10: 133-142 (1998)). Gould et al. developed a mouse/human chimeric IgE (MOv18-IgE) and IgG MOv18 (IgG1) specific for the ovarian cancer tumor-associated antigen folate binding protein (FBP). The protective activities of MOv18-IgE and MOv18-IgG1 were compared in a SCID mouse xenograft model of human ovarian carcinoma (IGROV1). The beneficial effects of MOv18-IgE were greater and of longer duration than those of MOv18-IgG1 demonstrating the superior anti-tumor effects of IgE antibodies (Gould, H J, et al., *Eur. J. Immunol.,* 29: 3527-3537 (1999)).

Recently Karagiannis et al. demonstrated monocyte-mediated IgE-dependent tumor cell killing by two distinct pathways, ADCC (antibody-dependent cell-mediated cytotoxicity) and ADCP (antibody-dependent cell-mediated phagocytosis), mediated through FcεRI and FcεRII (Karagiannis, S N, et al., *Cancer Immunol. Immunother.,* 57: 247-263 (2008) and Karagiannis, S N, et al., *J. Immunol.,* 179: 2832-2843 (2007)). This group also used this assay system to demonstrate that anti-Her2 IgE can activate monocytes to kill tumor cells in vitro via ADCC (Karragiannis P., et al., *Cancer Immunol. Immunother.,* 58: 915-930 (2009) Published on-line 22 Oct. 2008). Additional examples include Fu, et al. (*Clin. Exp. Immunol.,* 153:401-409, 2008) who demonstrated that antibodies of the IgE class isolated from pancreatic cancer patients mediate ADCC against cancer cells, and Spillner et al. (*Cancer Immunol. Immunother.,* 61: 1565-1573 (2012) who showed using monocytes, that cytotoxicity against the human epithelial carcinoma cell line A431 was increased up to 95% with anti-EGFR IgE when compared with anti-EGFR IgG in vitro.

In spite of the encouraging findings in the emerging field of AllergoOncology, a strong need continues for the development of novel therapeutics in the treatment of metastatic cancer.

SUMMARY OF THE INVENTION

The present invention provides novel IgE antibodies useful for inhibiting tumor growth and metastases. Provided are therapeutic monoclonal IgE antibodies comprising the human epsilon constant region and variable regions comprising the binding specificity for the tumor-associated antigen (TAA). Also provided are methods of reprogramming the activity of at least one host-derived, non-tumor cell located in the microenvironment of a primary solid tumor, thereby reversing the ability of the non-tumor cell to promote tumor growth and metastases. A method for treating metastatic carcinoma, for inhibiting the primary tumor from giving rise to metastases and for reducing the growth kinetics of a primary or metastatic tumor in a patient are provided.

In one embodiment the invention provides a method for reprogramming, the activity of at least one host-derived, non-tumor cell located in the microenvironment of a solid tumor in a patient wherein the ability of the non-tumor cell to mediate metastases of the tumor is inhibited, comprising the step of administering an IgE antibody specific for a tumor-associated antigen, wherein the antibody forms a ternary complex within the microenvironment of the tumor said ternary complex being comprised of the IgE antibody, the tumor-associated antigen, and a host-derived, non-tumor cell endogenous to the tumor environment wherein the antibody specifically binds to the tumor-associated antigen and an antibody receptor specific for IgE located on the surface of the host-derived non-tumor cell.

In another embodiment the invention provides a method for inhibiting metastasis of a solid tumor in a patient, the method comprising administering to the patient, an IgE antibody capable of forming a ternary complex within the microenvironment of the tumor, said ternary complex being comprised of the IgE antibody specific for a tumor-associated antigen, the tumor associated antigen and a host-derived, non-tumor cell endogenous to the tumor microenvironment, wherein the antibody specifically binds to the tumor-associated antigen and an antibody receptor specific for IgE located on the surface of the host-derived non-tumor cell and wherein upon the formation of the ternary complex, the ability of the non-tumor cell to mediate metastases of the tumor is inhibited.

DETAILED DESCRIPTION OF THE INVENTION

Figure 1:
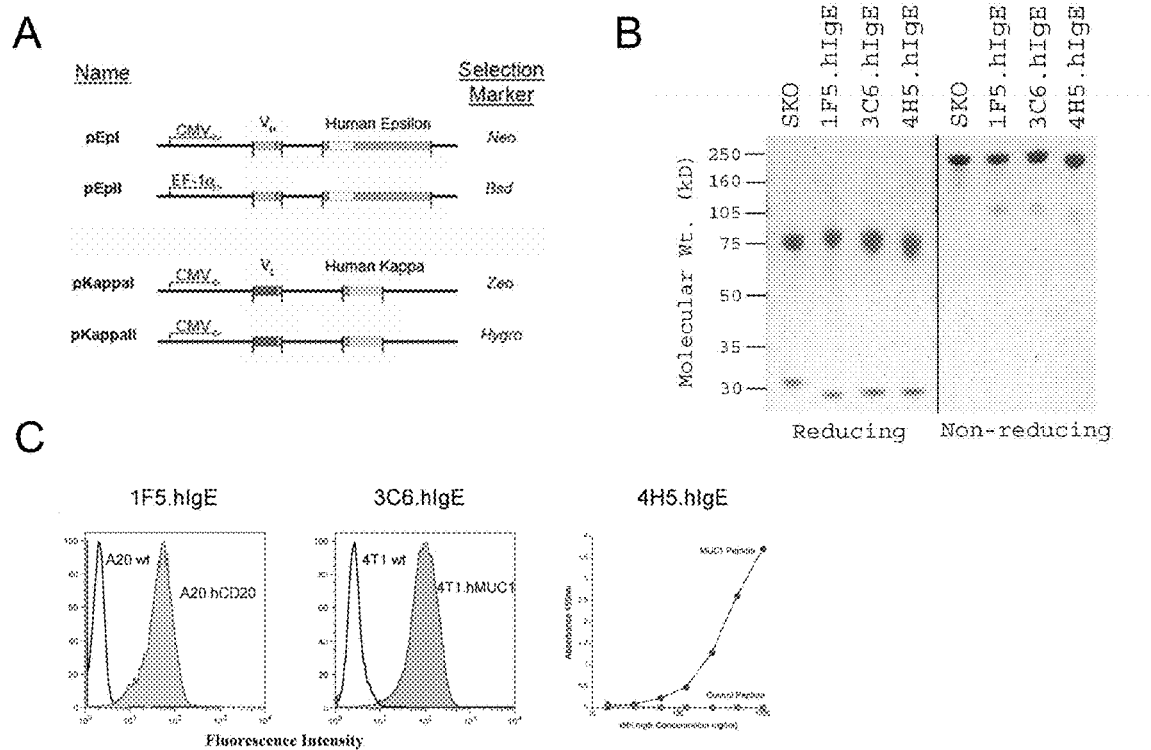
FIG. 1. Construction and antigen specificity of chimeric IgE antibodies. (A) Graphical representations of the vector constructs. The parent vectors were pcDNA 3.1/neomycin (pEpsilon I), pEF6/blastacidin (pEpsilon II), pcDNA 3.1/Zeocin (pKappa I), and pcDNA 3.1/Hygromycin (pKappa II). Heavy and light chain variable region genes were cloned from the hybridomas in Table 1, and inserted upstream of the human epsilon or human kappa constant region genes. (B) SDS-PAGE analysis. Chimeric IgE purified from transfected CHO-K1 clones, and control human IgE from myeloma cell line SKO-007 were separated by electrophoresis on a 4-12% gradient acrylamide gel and stained with Coomassie blue. (C) Analysis of antibody specificities. Histogram overlays depict FACS analysis of IgE binding to cell lines transfected with cognate antigen, compared to untransfected cell lines. 1F5.hIgE (anti-hCD20) bound A20 cells transfected with human CD20 cDNA, while 3C6.hIgE (anti-hMUC1, partially glycosylated form) detected human MUC1 on the mouse breast carcinoma cell line 4T-1 transfected with the hMUC1 cDNA. Line graph shows ELISA detection of a synthetic hMUC1 tandem repeat peptide (50mer) by 4H5.hIgE (anti-hMUC1 protein backbone). The control peptide was derived from the second extracellular loop of hCD20 (43mer).

The present invention provides novel IgE antibodies useful for inhibiting or preventing tumor growth and metastasis. Tumor metastasis is, in part, driven by the interplay of cytokines and bone marrow (myeloid) derived cells of the innate immune system present within the tumor microenvironment. Local expression of cytokines by tumor cells attracts myeloid suppressor cells, for example, into the tumor microenvironment, which in turn results in the release of additional cytokines by these cells. The cytokine milieu within the tumor microenvironment thus becomes complex, with dozens if not hundreds of cytokines and chemokines contributing to cancer-associated inflammation.

Tumor-associated myeloid-derived cells such as macrophages and mast cells that accumulate in the tumor microenvironment appear to be associated with tumor progression (DePalma et al., *Cancer Cell* 23(3): 277-286 (2013); Dalton et al., *Cancer Immunol Immunother* DOI 10.1007/s00262-012-1246-0 Published online Apr. 18, 2012). This association is modulated by the complex cytokine milieu found within the tumor microenvironment. For example, mammary carcinoma metastasis is enhanced by macrophages in the presence of type 2 cytokines (Ruffell B et al., *Trends Immunol.* 33: 119 (2012)). Also, in response to cytokines, other cells such as monocytes, granulocytes, and mast cells secrete proteolytic enzymes that modify the extracellular matrix (ECM), resulting in release of ECM-bound growth factors that facilitate metastasis (Hanahan D & Coussens L M, *Cancer Cell* 21: 309 (2012); Lu P, et al., *Cold Spring Harb. Perspect. Biol.*, 3: a005058 (2011)). It appears, therefore, that "chronically activated myeloid cells in neoplastic tissues support many of the hallmarks of cancer" (Coussens L M et al., *Science* 339: 286-291 (2013)); (Hanahan D & Coussens L M, *Cancer Cell* 21: 309 (2012)).

The inventors have unexpectedly discovered that the antibodies of the invention can inhibit metastases of primary solid tumors as well as secondary tumors and higher. Without being bound by theory, the IgE antibodies in accordance with the invention can reprogram host-derived non-tumor cells in the tumor microenvironment of a primary tumor such that tumor metastasis is inhibited or prevented from occurring. The invention is unique and unexpected in that it provides for modulating the behavior of a tumor cell through an intermediary, host derived cell. The end result is that a primary tumor will not metastasize. This is in stark contrast to heavily documented and well-known aspects of antibody-based cancer therapy wherein antibody-dependent cell-mediated cytoxicity (ADCC) and antibody-dependent cell-mediated phagocytosis (ADCP) are employed in the treatment of cancer to kill cancer cells directly Fu, et al. *Clin. Exp. Immunol.*, 153:401-409, 2008; Karagiannis P., et al., *Cancer Immunol. Immunother.*, 58: 915-930 (2009) Published on-line 22 Oct. 2008; Karagiannis, S N, et al., *Cancer Immunol. Immunother.*, 57: 247-263 (2008); and Karagiannis, S N, et al., *J. Immunol.*, 179: 2832-2843 (2007)).

In one embodiment of the invention, reprogramming of host-derived, non-tumor cells such as myeloid suppressor cells, occurs within the tumor microenvironment of a primary solid tumor. The reprogramming of the host-derived, non-tumor cells is mediated, for example, by cytokines and tumor-specific IgE antibodies within said tumor microenvironment after an effective amount of a tumor-specific IgE antibody is administered to the subject. In one embodiment, the reprogramming comprises the formation of a ternary complex within the tumor microenvironment. In one embodiment this ternary complex formed within the tumor microenvironment is comprised of an IgE antibody, a cell bearing the tumor-associated antigen on its surface such as a tumor cell or a soluble tumor-associated antigen, and a host derived, non-tumor cell. The antibody specifically binds to the tumor-associated antigen and an antibody receptor located on the surface of the host-derived non-tumor cell, after an effective amount of the antibody is administered to the subject.

The term "tumor microenvironment" or "tumor stroma" means the tissues, cells, molecules, and blood vessels that surround and feed a tumor cell. A tumor's microenvironment is dynamic and a tumor can change its microenvironment, and the microenvironment can affect how a tumor grows and spread.

In one embodiment the host-derived non-tumor cell (or cells) is an endogenous resident of the tumor microenvironment. As used herein the term "endogenous to the tumor microenvironment" which may be used interchangeably with the term "endogenous to the tumor stroma" means one or more cells of a dynamic compartment of cell types that intercalate or surround the tumor nest and includes, but is not limited to, connective tissue, vasculature, and inflammatory cells that will vary from time to time, but that also include tumor cells themselves. Other host-derived, non-tumor cells of the tumor stroma include fibroblasts and vascular cells, including, but not limited to, cells of mesenchymal origin (such as fibroblasts, vascular progenitor cells, endothelial cells, adipocytes and their precursors and vascular endothelial cells) and myeloid-derived cells of varying phenotypes including, but not limited to, mast cell, basophil, monocyte macrophage, eosinophil, neutrophil, dendritic cells, Langerhan's cells, platelets, and their progenitors and also infiltrating lymphocytes including CD4 and CD8 T cells and B cells. Allergic effector cells and/or myeloid suppressor cells are also collectively referred to herein as myeloid-derived cells or cells of myeloid lineage.

In a preferred embodiment, the antibody comprises human Fc epsilon constant regions. In one preferred embodiment, the IgE antibody is an antibody specific to CA125, folate binding protein (FBP), HER2/neu, MUC1, and PSA.

As used herein, a "subject" is a human patient or other animal such as another mammal with functional mast cells, basophils, neutrophils, eosinophils, monocytes, macrophages, dendritic cells, and Langerhans cells. In humans, all of these cells express the high affinity receptor for IgE (FIϵRI) for the administered IgE antibody of the invention.

In some instances the IgE antibodies of the invention can be used to inhibit spread from a primary tumor to a site that is distinct from the site of the primary tumor also known as metastases. These additional tumor sites are sometimes referred to as secondary, tertiary, quaternary, or higher tumor sites when they are the result of metastases from a primary tumor site. Primary tumors release circulating cancer cells that first must set up microenvironments within various tissues and organs such as liver, lungs, and bone. These eventually give rise to clinically and radiographically apparent metastases. Unlike IgG antibodies, which primarily stay within the vascular compartment, IgE antibodies migrate out of the vascular space to every tissue in the body.

In one embodiment, the reprogramming of host-derived, non-tumor cells endogenous to the tumor microenvironment occurs within the microenvironment of a secondary, tertiary, quaternary, or higher tumor site formed by circulating cancer cells. In a second embodiment, cell reprogramming is mediated by tumor-specific antibodies within said secondary, tertiary, quaternary, or higher tumor microenvironment, wherein an effective amount of a tumor-specific antibody is administered to the subject.

In one embodiment, the host-derived non-tumor cell is a myeloid derived suppressor cell that is endogenous to the tumor microenvironment. In a preferred embodiment, myeloid derived suppressor cells are independently selected from mast cells, basophils, neutrophils, eosinophils, monocytes, macrophages, dendritic cells, and Langerhans cells. In one embodiment, the host-derived non-tumor cell is of mesenchymal origin and are independently selected from fibroblasts, vascular progenitor cells, endothelial cells, adipocytes and their precursors.

The inventors have also discovered that the antibodies of the invention can mediate tumor rejection. The effect was shown to be mediated by myeloid-derived cells activated by IgE and tumor-associated cell surface antigens. The killing of tumors was the result of local effects of IgE antibodies, the presence of myeloid-derived cells in the environment, and cytokines chemotactic for macrophages, eosinophils. In one embodiment, the IgE antibodies of the invention can be used to induce tumor cell death at secondary, tertiary, quaternary, or higher microenvironment sites after metastasis has occurred. In a second embodiment, tumor cell death at secondary, tertiary, quaternary, or higher microenvironment sites is mediated by altering the pattern of cytokines present therein and alteration in the activation state of non-tumor cells, all in response to tumor-specific antibodies within said microenvironments. In a preferred embodiment, tumor cell death requires ternary complex formation within said microenvironments, the ternary complex being comprised of an IgE antibody, a tumor cell bearing the target antigen, and a non-tumor cell. Specifically the IgE antibody specifically binds to an antigen located on the surface of the tumor cell and an antibody receptor located on the surface of the non-tumor cell, wherein an effective amount of the antibody is administered to the subject. In another embodiment, the non-tumor cell is myeloid derived suppressor cell. In a preferred embodiment, the myeloid derived suppressor cells is independently selected from mast cells, basophils, neutrophils, eosinophils, monocytes, macrophages, dendritic cells, and Langerhans cells. In a preferred embodiment, the IgE antibody is anti-MUC1 IgE.

The inventors have further discovered that the antibodies of the invention can be used to reduce the growth kinetics of a primary solid tumor or a metastasized cell or tumor in a patient. In one embodiment, the reprogramming of myeloid derived cells occurs within the tumor microenvironment of a primary solid tumor or a metastasized group of cells. In a second embodiment, the reprogramming is mediated by tumor-specific antibodies within said tumor microenvironment, wherein an effective amount of a tumor-specific antibody is administered to the subject. In a preferred embodiment, the reprogramming requires ternary complex formation within the microenvironment of a solid tumor or metastasized cells or tumor, said ternary complex being comprised of an antibody, a tumor cell of the solid or metastasized cell or tumor, and a non-tumor cell, wherein the antibody specifically binds to an antigen located on the surface of the tumor cell and an antibody receptor located on the surface of the non-tumor cell, and wherein an effective amount of the antibody is administered to the subject. In another embodiment, the non-tumor cell is a myeloid-derived cell. In a preferred embodiment, the myeloid-derived cell is of myeloid lineage independently selected from mast cells, myeloblasts, basophils, neutrophils, eosinophils, monocytes, macrophages, dendritic cells, and Langerhans cells. In a preferred embodiment, the antibody is IgE. In a more preferred embodiment, the IgE antibody is anti-MUC1 IgE. As used herein, a "subject" is a human patient or other animal with functional mast cells, myeloblasts, basophils, neutrophils, eosinophils, monocytes, macrophages, dendritic cells, and Langerhans cells with receptor affinity for the administered IgE antibody of the invention.

A reduction in the growth kinetics of a primary solid tumor or a metastasized cell or tumor as used herein is defined to mean that which is as understood in the art. For example, a reduction in growth kinetics means a reduction in the exponential growth, specific growth rate, or doubling time of a primary solid tumor, metastasized cell, or metastasized tumor relative to the exponential growth, specific growth rate, or doubling time normally observed in vivo or in vitro for a given tumor type.

A "therapeutic IgE antibody" of the invention (also referred to herein as a "monoclonal IgE antibody of the invention") is a monoclonal antibody that comprises the human epsilon (ε) constant region and also comprises variable regions comprising at least one antigen binding region specific for a tumor-associated antigen (TAA) that is a cell surface antigen or a soluble cancer antigen located in the tumor microenvironment or otherwise in close proximity to the tumor being treated. It is believed that the therapeutic dosage of the IgE antibody of the invention will be much lower than that associated with IgG classes of antibody therapy against cancer (e.g. trastuzumab (HERCEPTIN®) and rituximab (RITUXAN®)) not only due to the high affinity of IgE to the FcεRI but also because the methods of the invention that comprise reprogramming of one or more host-derived non-tumor cells endogenous to the tumor microenvironment appears to have a cascading effect within the tumor environment which facilitates inhibition of metastases of a solid tumor. This cascading effect means that IgE antibody in accordance with the invention need not be administered to mediate pharmacologic effects to the target antigens and thus for example there is no need to saturate CD20 or HER2/neu receptors, for example, as is necessary with conventional IgG based monoclonal cancer therapy.

The term "tumor-associated antigen" (TAA) as used herein can be any type of cancer antigen that may be associated with a tumor as is known in the art and includes antigens found on the cell surface of cells including tumor cells as well as soluble cancer antigens. Such antigens include, but are not limited to cancer-associated fibroblasts (CAFs), tumor endothelial cells (TEC) and tumor-associated macrophages (TAM). Examples of cancer-associated fibroblasts (CAFs) include but are not limited to: carbonic anhydrase IX (CAIX); fibroblast activation protein alpha (FAPα); and matrix metalloproteinases (MMPs) including MMP-2 and MMP-9. Examples of Tumor endothelial cell (TECs) target antigens include, but are not limited to vascular endothelial growth factor (VEGF) including VEGFR-1, 2, and 3; CD-105 (endoglin), tumor endothelia markers (TEMs) including TEM1 and TEM8; MMP-2; Survivin; and prostate-specific membrane antigen (PMSA). Examples of tumor associated macrophage antigens include, but are not limited to: CD105; MMP-9; VEGFR-1, 2, 3 and TEM8.

In one embodiment, the therapeutic IgE antibody may be specific for cancer antigens located on tumor cells, for example, VEGFR-2, MMPs, Survivin, TEM8 and PMSA. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. A cancer antigen can also be a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen.

Other cancer antigens include but are not limited to mucin-1 protein or peptide (MUC-1) that is found on all human adenocarcinomas: pancreas, colon, breast, ovarian, lung, prostate, head and neck, including multiple myelomas and some B cell lymphomas; mutated B-Raf antigen, which is associated with melanoma and colon cancer; human epidermal growth factor receptor-2 (HER-2/neu) antigen; epidermal growth factor receptor (EGFR) antigen associated lung cancer, head and neck cancer, colon cancer, colorectal cancer, breast cancer, prostate cancer, gastric cancer, ovarian cancer, brain cancer and bladder cancer; prostate-specific antigen (PSA) and/or prostate-specific membrane antigen (PSMA) that are prevalently expressed in androgen-independent prostate cancers; gp-100 (Glycoprotein 100) associated with melanoma carcinoembryonic (CEA) antigen; carbohydrate antigen 19.9 (CA 19.9) related to the Lewis A blood group substance and is associated with colorectal cancers; and a melanoma cancer antigen such as MART-1.

Other antigens include mesothelin, folate binding protein (FBP), carbohydrate antigen 125 (CA-125) and melanoma associated antigens such as NYESO 1.

In one embodiment, the cancer antigen is a soluble cancer antigen. In a preferred embodiment the tumor-associated target antigen is a cell surface antigen located on the surface of a tumor cells. In one preferred embodiment the tumor associated antigen is selected from CA125, folate binding protein (FBP), HER2/neu, MUC1, and PSA.

The terms "monoclonal antibody" or "monoclonal antibodies" as used herein refer to a preparation of antibodies of single molecular composition. A monoclonal antibody composition displays a single binding specificity and affinity for a particular epitope. The monoclonal antibodies of the present invention are preferably chimeric, humanized, or fully human in order to bind human Fc epsilon receptors when the subject host is a human. Humanized and fully human antibodies are also useful in reducing immunogenicity toward the murine components of, for example, a chimeric antibody, when the host subject is human. Monoclonal antibodies may be prepared by standard techniques including, but not limited to, recombinantly and synthetically.

The term "chimeric monoclonal antibody" refers to antibodies displaying a single binding specificity, which have one or more regions derived from one antibody and one or more regions derived from another antibody. In one embodiment of the invention, the constant regions are derived from the human epsilon (ε) constant region (heavy chain) and human kappa or lambda (light chain) constant regions. The variable regions of a chimeric IgE monoclonal antibody of the invention are typically of non-human origin such as from rodents, for example, mouse (murine), rabbit, rat or hamster.

As used herein, "humanized" monoclonal antibodies comprise constant regions that are derived from human epsilon constant region (heavy chain) and human kappa or lambda (light chain) constant regions. The variable regions of the antibodies preferably comprise a framework of human origin and antigen binding regions (CDRs) of non-human origin.

Fully human or human-like antibodies may be produced through vaccination of genetically engineered animals such as mouse lines produced at Abgenix Inc. (Thousand Oaks, Calif.) and MedaRex (Princeton, N.J.) which contain the human immunoglobulin genetic repertoire and produce fully human antibodies in response to vaccination. Further, the use of phage display libraries incorporating the coding regions of human variable regions which can be identified and selected in an antigen-screening assay to produce a human immunoglobulin variable region binding to a target antigen.

The term "antigen binding region" refers to that portion of an antibody of the invention which contains the amino acid residues that interact with an antigen and confer on the antibody its specificity and affinity for the antigen. The antibody region includes the "framework" amino acid residues necessary to maintain the proper confirmation of the antigen binding residues.

An "antigen" is a molecule or portion of a molecule capable of being bound by an antibody, which is additionally capable of inducing an animal to produce antibody capable of binding to an epitope of that antigen. An antigen can have one or more epitopes that are the same or different. In a preferred embodiment, the antibodies of the invention are specific for a single epitope. In one embodiment, the antigen is a capable of being bound by an IgE antibody of the invention to form an immune complex that in combination with a myeloid effector cell is capable of reprogramming the tumor microenvironment to inhibit or prevent tumor metastasis. In one embodiment, the antigen, on its own, may not be capable of stimulating an immune response for any number of reasons, for example, the antigen is a "self" antigen, not normally recognized by the immune system as requiring response or the immune system has otherwise become tolerant to the antigen and does not mount an immune response. In another embodiment, the antigen is MUC1.

The term "epitope" is meant to refer to that portion of an antigen capable of being recognized by and bound by an antibody at one or more of the antibody's binding regions. Epitopes generally comprise chemically active surface groupings of molecules such as amino acids or sugar side chains and have specific three dimensional structure characteristics as well as specific charge characteristics. In one embodiment, an epitope of an antigen is a repetitive epitope. In one embodiment an epitope of an antigen is a non-repetitive epitope.

A "ternary complex" is a complex formed in the microenvironment of a tumor comprised of an IgE antibody of the invention, a tumor-associated target antigen, and a host-derived non-tumor cell, wherein the antibody specifically binds to a tumor associated antigen and an antibody receptor located on the surface of the non-tumor cell.

In one preferred embodiment, the antigen is CA-125, folate binding protein (FBP), HER2/neu, MUC1 or PSA. In one embodiment, the non-tumor cell is an effector cell. In one embodiment, the effector cell is an allergic and/or anti-parasitic effector cell of myeloid lineage. In a preferred embodiment, the IgE is anti-MUC1 IgE. In a preferred embodiment, the antibody receptor is FcεRI.

In one embodiment, a ternary complex includes an IgE antibody bound to a soluble cancer antigen and an antibody receptor located on the surface of a host-derived non-tumor cell. In a preferred embodiment the ternary complex includes an IgE antibody bound to a tumor-associated target antigen expressed on the surface of the tumor cell and an FcεRI located on a host-derived, non-tumor cell endogenous to the tumor microenvironment.

Methods for raising antibodies, such as murine antibodies to an antigen, and for determining if a selected antibody binds to a unique antigen epitope are well known in the art.

Screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Many means are known in the art for detecting binding in an immunoassay and are within the scope of the present invention.

For preparation of monoclonal antibodies, any technique that provides for the production of antibody molecules by continuous cell lines in culture may be used (see, e.g., Antibodies—A Laboratory Manual, Harlow and Lane, eds., Cold Spring Harbor Laboratory Press: Cold Spring Harbor, N.Y., 1988). These include but are not limited to the hybridoma technique originally developed by Kohler and Milstein (1975, *Nature* 256:495-497), as well as the trioma technique, the human B-cell hybridoma technique (Kozbor et al., 1983, *Immunology Today*, 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.*, 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, *J. Bacteriol.* 159: 870; Neuberger et al., 1984, *Nature* 312:604-608; Takeda et al., 1985, *Nature* 314: 452-454) by splicing the genes from a mouse antibody molecule specific for a polypeptide together with genes from a human antibody molecule of appropriate biological activity can be used; such antibodies are within the scope of this invention.

In one embodiment, the antibody of the invention is an IgE monoclonal antibody comprising a nucleic acid sequence selected from a heavy chain variable region encoded by a nucleic acid sequence comprising SEQ ID NO: 1; a light chain variable region encoded by a nucleic acid sequence comprising SEQ ID NO: 2 and any combination thereof and wherein the heavy and or light chain or both is grafted onto human Ig kappa light chain and epsilon heavy chain genes.

In one embodiment the antibody of the invention is an IgE monoclonal antibody comprising a nucleic acid sequence selected from a heavy chain variable region encoded by the nucleic acid of SEQ ID NO: 3; a light chain variable region encoded by the nucleic acid of SEQ ID NO: 4 and any combination thereof and wherein the heavy and or light chain or both is grafted onto human Ig kappa light chain and epsilon heavy chain genes.

In one embodiment, the invention provides a monoclonal antibody, 3C6.hIgE, comprising variable regions of the light and heavy chain of IgG cloned from the VU-3C6 hybridoma, and grafted onto human Ig kappa light chain and epsilon heavy chain genes. VU-3C6 targets human mucin 1 (hMUC1), a mucin overexpressed on tumors arising from glandular epithelium. In one embodiment, the invention comprises the IgE antibody, 4H5hIgE, which is specific to an isoform of MUC1 different from the MUC1 isoform that 3C6.hIgE is specific to.

In one embodiment, the antibody of the invention is the monoclonal antibody 3C6.hIgE comprising a heavy chain variable region encoded by a nucleic acid sequence comprising SEQ ID NO: 1; a light chain variable region encoded by a nucleic acid sequence comprising SEQ ID NO: 2.

In one embodiment the antibody of the invention is the monoclonal antibody 4H5hIgE. The antibody 4H5.hIgE has a heavy chain variable region encoded by the nucleic acid of SEQ ID NO: 3 and a light chain variable region encoded by the nucleic acid of SEQ ID NO: 4 and grafted onto human Ig kappa light chain and epsilon heavy chain genes.

In one embodiment, the antibody of the invention is an IgE monoclonal antibody specific for an epitope of MUC1. In one embodiment, the antibody of the invention is specific for the epitope of MUC1 comprising amino acids STAPPAHGVTSAPDTRPAPG [SEQ ID NO: 5] of MUC1. The exact epitope lies in one of the 20 amino acid repeats that characterize the external domain of MUC1. In one embodiment, the antibody of the invention is capable of binding MUC1 at the epitope defined at STAPPAHGVTSAPDTRPAPG [SEQ ID NO: 5].

In one embodiment, antibodies in accordance with the present invention are expressed by a positive transfectoma which is identified by enzyme-linked immunosorbent assay (ELISA) and Western Blot. The positive transfectoma will be cloned by limited dilution for highest productivity and selected for antibody production. As used herein a "transfectoma" includes recombinant eukaryotic host cells expressing the antibody, such as Chinese hamster ovary (CHO) cells and NS/O myeloma cells. Such transfectoma methodology is well known in the art (Morrison, S. (1985) *Science*, 229:1202). Previously published methodology used to generate mouse/human chimeric or humanized antibodies has yielded the successful production of various human chimeric antibodies or antibody fusion proteins (Helguera G, Penichet M L., *Methods Mol. Med.* (2005)109:347-74).

In general, chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See Robinson et al., International Patent Publication PCT/US86/02269; Akira, et al., European Patent Application 184,187; Taniguchi, M., European Patent Application 171, 496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science, 240:1041-1043); Liu et al. (1987) PNAS, 84:3439-3443; Liu et al., 1987, J. Immunol., 139:3521-3526; Sun et al. (1987) PNAS, 84:214-218; Nishimura et al., 1987, Canc. Res., 47:999-1005; Wood et al. (1985) Nature, 314:446-449; and Shaw et al., 1988, J. Natl Cancer Inst., 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, Science, 229:1202-1207 and by Oi et al., 1986, BioTechniques, 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution (U.S. Pat. No. 5,225,539; Jones et al. 1986 Nature, 321:552-525; Verhoeyan et al. 1988 Science, 239: 1534; and Beidler et al. 1988 J. Immunol., 141:4053-4060).

In one embodiment, the immunogenicity of an IgE monoclonal antibody of the invention is reduced as compared to, for example, the parent antibody from which it was derived, using various strategies. For example, a chimeric IgE monoclonal antibody of the invention comprising human Fcε constant regions and murine variable regions may be rendered less immunogenic to the human subject by genetically engineering humanized antibodies which comprise constant regions that are derived from human Fcε and variable regions that comprise a framework of human origin and antigen binding regions of non-human origin that maintain the same antigen specificity as that of the parent chimeric antibody. Alternatively, fully human or human like antibodies comprising the same antigen specificity as the parent chimeric IgE monoclonal antibodies may also be genetically engineered using known procedures.

Other processes for reducing the immunogenicity of IgE monoclonal antibodies of the invention include, but are not limited to, processes such as DE-IMMUNIZATION™ (Biovation Ltd., Aberdeen, United Kingdom and Merck KgaA, Darmstadt, Germany). This technology is a process that identifies murine epitopes present on murine or chimeric monoclonal antibodies that might cause immunogenicity in humans such as "human anti-mouse antibody" (HAMA) or "human anti-chimeric antibody" (HACA). This process further genetically alters these epitopes to avoid or at least reduce immunogenicity as compared to antibodies that have not been subjected to this process.

Other methods of reducing immunogenicity of monoclonal antibodies (Lazar et al., Mol Immunol., 44, 1986-1998 (2007)) identifies framework and antigen binding region peptides or conformational motifs that may activate T-helper cells resulting in HAMA or HACA responses. Using this method a novel quantitative paradigm is used to determine the "humanness" of murine variable regions and murine regions of low human identity can be substituted for regions of higher human identity thereby reducing immunogenicity of the antibody.

As used herein the induction of an IgE-mediated immune response includes one or more of the following:
  i) Ternary complex formation within a tumor microenvironment or on a tumor cell comprising binding of an IgE antibody to a myeloid-derived cell and to a tumor-specific antigen such that reprogramming of the myeloid-derived cell inhibits or prevents tumor metastasis;
  ii) Hypersensitivity against the antigen/IgE immune complex particularly in the tumor microenvironment as evidenced by degranulation of mast cells and basophils bound to such immune complex via IgE antibody receptors FcεRI and/or FcεRII and the release of histamine, for example;
  iii) Direct targeting of tumor cells via ADCC immune responses, ADCP immune responses or both ADCC and ADCP immune responses against the antigen/IgE immune complex particularly in the tumor microenvironment as evidenced by the stimulation of eosinophils, mast cells, basophils, and other cells to release pro-inflammatory cytokines, proteases and vasoactive lipid mediators (e.g. leukotrienes, prostaglandin D2, and platelet activating factor when bound to the antigen/IgE immune complex via IgE antibody receptors FcεRI and FcεRII;
  iv) a cellular response as evidenced in part by the production of T-cells that are specific for the antigen, the antigen/IgE antibody immune complex, or a peptide of the antigen complexed with MHC;
  v) a Th1/Tc1 immune response in response to challenge with the antigen/IgE antibody immune complex as evidenced, for example, by the production of CD8 IFN gamma positive T cells in response to the tumor antigen and tumor;
  vi) a humoral response as evidenced by production of antibodies against the antigen or the antigen/IgE immune complex.

As used herein, an "effective amount" of an IgE monoclonal antibody of the invention is that amount sufficient to recognize and bind the epitope of the TAA that is a cell surface antigen and induce, elicit, or enhance the referenced immune response in accordance with the invention.

The invention also provides a method for inducing an IgE-mediated immune response against a cell surface antigen on a circulating tumor cell in a subject capable of mounting such a response. This comprises administering to the subject an effective amount of an IgE monoclonal antibody that specifically binds an epitope of the surface of a circulating tumor cell antigen wherein an IgE mediated immune response against the tumor results.

As used herein the induction of an IgE-mediated immune response triggered by a cell surface antigen on a circulating tumor cell, or clinically unapparent metastases is evidenced, in part, by any one of the following:
  i) the inhibition of tumor growth and/or the facilitation of tumor destruction, in whole or in part, resulting from reprogramming of myeloid derived cells in the tumor microenvironment;
  ii) acute inflammation in the tumor environment and subsequent tumor growth inhibition and or destruction via effector cells bearing human Fc epsilon receptors able to bind-monoclonal IgE antibody and direct ADCC immune responses, ADCP immune responses or both ADCC and ADCP immune responses reactions to the antigen in the microenvironment;

iii) secondary T cell responses evidenced by the appearance of T-cells displaying specificity for the target tumor antigen or secondarily additional antigens derived from the tumor and expressed in the context of MHC on the tumor cell resulting in tumor growth inhibition or lysis and destruction; or iv) T cell response against the tumor evidenced by the production of T cells against other antigens associated with tumor cells that have been lysed as above in (ii).

The invention also provides methods of inducing direct IgE-mediated ADCC immune responses, ADCP immune responses, or both ADCC and ADCP immune responses to a TAA on the surface of a primary tumor, or to a TAA on the surface of circulating metastasized tumor cell in a subject capable of mounting such an immune response comprising administering to the subject an effective amount of an IgE monoclonal antibody that specifically binds a single epitope of the circulating antigen wherein an IgE mediated ADCC immune response and possibly or optionally an ADCP immune response against the antigen is elicited. In a preferred embodiment, the ADCC immune response and possibly or optionally an ADCP immune response is elicited in the microenvironment of a tumor or tumor cell. In another embodiment the ADCC immune response and possibly or optionally an ADCP immune response is capable of causing the lysing and killing of tumor cells within the tumor microenvironment or at the tumor cell via bystander effects.

The invention also provides a method for the treatment of cancer associated with the antigen to which the antibody of the invention is specific, by administering a composition comprising an IgE monoclonal antibody of the invention that specifically binds at least one single epitope of a tumor-associated antigen. Such cancers include but are not limited to pancreatic cancer, gastric cancer (cancer of the gastrointestinal tract), colorectal cancer, and lung cancer. Other types of cancers that may be treated by the methods of the invention include but are not limited to: osteosarcoma, esophageal cancer, lung cancer, mesotheliona, liver cancer, gastric cancer, pancreatic cancer, colorectal cancer, rectal cancer, colic cancer, ureteral tumor, brain tumor, gallbladder cancer, cholangioma, bile duct cancer, renal cancer, breast cancer, urinary bladder cancer, ovarian cancer, uterocervical cancer, prostatic cancer, thyroid cancer, testicle tumor, Kaposi's sarcoma, maxillary cancer, tongue cancer, lip cancer, oral cancer, laryngeal cancer, pharyngeal cancer, myosarcoma, skin cancer and the like.

In one embodiment, the invention provides a method of treating cancers of epithelial origin in a subject by administering to the subject a therapeutic IgE monoclonal antibody of the invention that specifically binds an epitope of MUC1. In a preferred embodiment, the therapeutic IgE monoclonal antibody of the invention that binds a single epitope of MUC1 inhibits or prevents tumor metastasis by reprogramming the tumor microenvironment in the primary tumor, or prevents establishment of clinically or radiographically apparent metastases by interfering with the establishment of a network of host-derived, myeloid cells that promote tumor growth outside of their tissue of origin.

In one embodiment, the term "reprogramming the tumor microenvironment" means the net effect of antigen bound IgE on host-derived, resident myeloid cells in a tumor, or allergic effector cells subsequently drawn into the tumor, on tumor growth and metastases. Once bound to both the antigen, and the high affinity FceRI on a host derived cell, located in the region of the tumor microenvironment, the tumor behavior is changed such that the tumor will not form metastasis. In one embodiment, reprogramming the tumor microenvironment is facilitated by the formation of a ternary complex. In one embodiment, the ternary complex is comprised of the IgE antibody, an effector cell, and a tumor-associated antigen.

The present invention also provides pharmaceutical compositions. Such compositions comprise a therapeutically effective amount of an antibody of the invention and a pharmaceutically acceptable carrier. In one preferred embodiment, the pharmaceutical composition comprises a therapeutic IgE monoclonal antibody of the invention that specifically binds a single epitope of MUC1.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

In accordance with a method of the invention compositions comprising the IgE monoclonal antibody of the invention may be administered to the patient by any immunologically suitable route. For example, the antibody may be introduced into the patient by an intravenous, subcutaneous, intraperitoneal, intrathecal, intravesical, intradermal, intramuscular, or intralymphatic routes. The composition may be in solution, tablet, aerosol, or multi-phase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The invention should not be limited to any particular method of introducing the binding agent into the patient.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the composition of the invention which will be effective in the treatment, inhibition and prevention of tumor metastasis associated with the antigen to which the antibody of the invention is specific can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For the antibodies of the invention, the dosage administered to a patient is typically 0.001 µg/kg to 1 mg/kg of the patient's body weight. Preferably, the dosage administered to a patient is between 0.01 µg/kg and 0.1 mg/kg of the patient's body weight, more preferably 0.02 µg/kg to 20 µg/kg of the patient's body weight. Generally, the IgE monoclonal antibodies of the invention have a much higher affinity for the Fcε R (as compared to IgG antibodies, for example) and longer half-life within the human body than antibodies from other species. Thus, lower dosages of the antibodies of the invention and less frequent administration is often possible.

Pharmaceutical compositions of the invention also can be administered in combination therapy, i.e. combined with other agents. For example a combination therapy can include a composition of the present invention with at least one anti-tumor agent, efficacy enhancing agent, and/or safety enhancing agent.

The pharmaceutical compositions of the present invention have in vitro and in vivo diagnostic and therapeutic utilities. For example, these molecules can be administered to cells in culture, e.g., in vitro or ex vivo, or in a subject, e.g., in vivo, to treat cancer. As used herein, the term "subject" is intended to include human and non-human animals. A preferred subject is a human patient with cancer. As used herein the terms "treat" "treating" and "treatment" of cancer includes: inhibiting tumor metastasis in a patient, inhibiting the onset of cancer in a patient; eliminating or reducing tumor burden in a patient; prolonging survival in a cancer patient; prolonging the remission period in a cancer patient following initial treatment with chemotherapy and/or surgery; and/or prolonging any period between cancer remission and cancer relapse in a patient.

As used herein "inhibit", "inhibition" or "inhibiting" in the context of the invention means to slow, hinder, restrain reduce or prevent. For example, "inhibiting metastasis" of a primary tumor cell as that term is used herein means to slow, hinder, restrain, reduce or prevent the primary tumor cell from metastasizing.

As used herein, "administering" refers to any action that results in exposing or contacting a composition containing an antibody of the invention with a pre-determined cell, cells, or tissue, typically mammalian. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

When used for therapy for the treatment of cancer, the antibodies of the invention are administered to the patient in therapeutically effective amounts (i.e. amounts needed to treat clinically apparent tumors, or prevent the appearance of clinically apparent tumor, either at the original site or a distant site, at some time point in the future. The antibodies of the invention and the pharmaceutical compositions containing them will normally be administered parenterally, when possible, at the target cell site, or intravenously.

In another embodiment, the IgE antibodies of the invention can be co-administered with a second therapeutic agent, e.g., a chemotherapeutic agent. Such therapeutic agents include, among others, anti-neoplastic agents such as doxorubicin, cisplatin, bleomycin sulfate, paclitaxel, carmustine, chlorambucil, and cyclophosphamide. These agents by themselves, are only effective at levels which are toxic or subtoxic to a patient. Furthermore, these agents are thought not to be curative in common solid tumors which have spread outside of their tissue of origin. By co-administering tumor specific IgE antibodies and common chemotherapy agents, the goal will be to enhance the activity of the chemotherapy agent, by preventing the emergence of chemotherapy resistance, the latter being a product of host derived, non-tumor cells in the microenvironment.

Pharmaceutical compositions of the present invention can include one or more further chemotherapeutic agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolamide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodophyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-.alpha.), monoclonal antibodies (e.g., trastuzumab and bevacizumab), recombinant toxins and immunotoxins (e.g., recombinant cholera toxin-B and TP-38), cancer gene therapies, physical therapies (e.g., hyperthermia, radiation therapy, and surgery) and cancer vaccines (e.g., vaccine against telomerase).

The present invention is further illustrated by the following non-limiting examples.

EXAMPLES

Example 1

Creation of Chimeric IgE Gene Vectors

Hybridomas VU-3C6 and VU-4H5 were raised against two different isoforms of human mucin 1 (hMUC-1), a mucin overexpressed on tumors arising from glandular epithelium. Antibody variable gene segments were cloned from each hybridoma, and grafted onto human kappa light chain and epsilon heavy chain gene segments using standard procedures. Kappa cDNA from human peripheral lymphocytes was cloned and then compared the sequence to the data base sequences (e.g. GenBank: J00241.1). The epsilon constant region cDNA, was cloned from an IgE-expressing hybridoma (SKO-007, ATCC CRL 8033-1) and compared to the genomic sequence in the data base (e.g. GenBank: J00222.1). The final IgE mouse-human chimeric antibodies were designated 3C6.hIgE and 4H5.hIgE. The final plasmids are shown in FIG. 1A.

The 1F5 hybridoma targets human CD20 (hCD20), a pan-B cell marker and important therapeutic target for treatment of B cell lymphomas and several autoimmune diseases. Antibody variable gene segments were cloned from the 1F5 hybridoma, and grafted onto human Ig kappa light chain and epsilon heavy chain genes using standard procedure as described above. The final IgE chimeric antibody was designated 1F5.hIgE. The final plasmid is shown in FIG. 1A.

The final plasmids were transfected into CHO-K1 cells (American Type Culture Collection (ATCC), Manassas, Va.) for antibody production and purification. Human IgE was purified by Fast Protein Liquid Chromatography (FPLC), using an anti-hIgE affinity column. FIG. 1B shows the SDS-PAGE comparison of the purified chimeric IgEs, to a human IgE isotype control (IgE from human myeloma SKO-007, purified in a similar fashion). All three samples of chimeric antibody are pure, with minor size differences compared to control hIgE (likely due to different glycosylation patterns). Under reducing conditions, the epsilon heavy chain migrates at 75 kDa, unlike the gamma heavy chain, which migrates as a 50 kDa polypeptide.

The purified antibodies were tested for their ability to bind their respective native antigen (i.e. CD20 and MUC1). As analyzed via flow cytometry, 1F5.hIgE bound the A20 mouse B cell lymphoma transfected with human CD20, but not the wild type cell line (FIG. 1C left panel). Similarly, 3C6.hIgE bound to 4T1 murine breast cancer cells transfected with human MUC1, but not to untransfected 4T1 cells (FIG. 1C center panel). 4H5.hIgE bound to a 50-mer peptide derived from the tandem repeat, extracellular domain of human MUC-1, as detected by ELISA, but did not bind a control peptide (FIG. 1C right panel). Thus, the use of the human epsilon and kappa constant regions, as well as the production and purification protocol, did not affect antigen recognition by the variable regions of the original mouse antibodies.

Example 2

IgE-Mediated Tumor Cytotoxicity by 1F5.hIgE (Anti-hCD20)

To determine if the anti-hCD20 chimeric antibody 1F5.hIgE had a functional IgE Fc region, we investigated its ability to activate cord blood derived mast cells (CBMCs). Using interleukin-8 (IL-8) production as a measure of CBMC activation, we observed that CBMCs pre-coated with 1F5.hIgE produced IL-8 in the presence of hCD20-transfected mouse B cells (A20.hCD20), but not untransfected cells. Similarly, only CBMCs coated with anti-hCD20 IgE (1F5.hIgE) responded to the hCD20$^+$ human B cell OCI-Ly8, while CBMCs coated with a control IgE (SKO) failed to produce IL-8 under these conditions. These data demonstrate that 1F5.hIgE activates mast cells in an antigen-dependent and antigen-specific manner.

Mast Cells and IgE-Mediated Tumor Cytotoxicity

To test for potential cytotoxic effects mediated by tumor specific IgE, we focused on effector cells known to express and respond to the high affinity IgE receptor, FcϵRI. Previous investigators reported tumor cytotoxicity mediated by human monocytes and tumor-specific IgE (Karagiannis et al. (2003). *Eur J Immunol* 33:1030-1040). We observed similar results using U937 monocytes in our system. In this report, we focus on data obtained using human mast cells and eosinophils; two cell types involved in the pathogenesis and tissue damage observed in allergy and asthma (Rothenberg et al., 2006 *Nat Rev Immunol* 8:205-217; Gould and Sutton. 2008 *Nat Rev Immunol* 8:205-217; Tsai et al., 2005 *Chem Immunol Allergy* 87:179-197. Mast cells were of particular interest because they reside in the tissues where tumors arise, express high levels of FcϵRI, and when activated trigger a coordinated inflammatory response that recruits eosinophils, neutrophils and other effectors that may potentially mediate tumor regression (Theoharides and Conti, 2004 *Trends Immunol* 25:235-241). Previously, mast cells have been shown to exert tumoricidal effects via TNF and the peroxidase system (Henderson et al., 1981 *J Exp Med* 153:520-533; Benyon et al., 1991 *J Immunol* 147:2253-2258; Ozdemir, O. 2007 *J Immunol Methods* 319:98-103).

Figure 2:
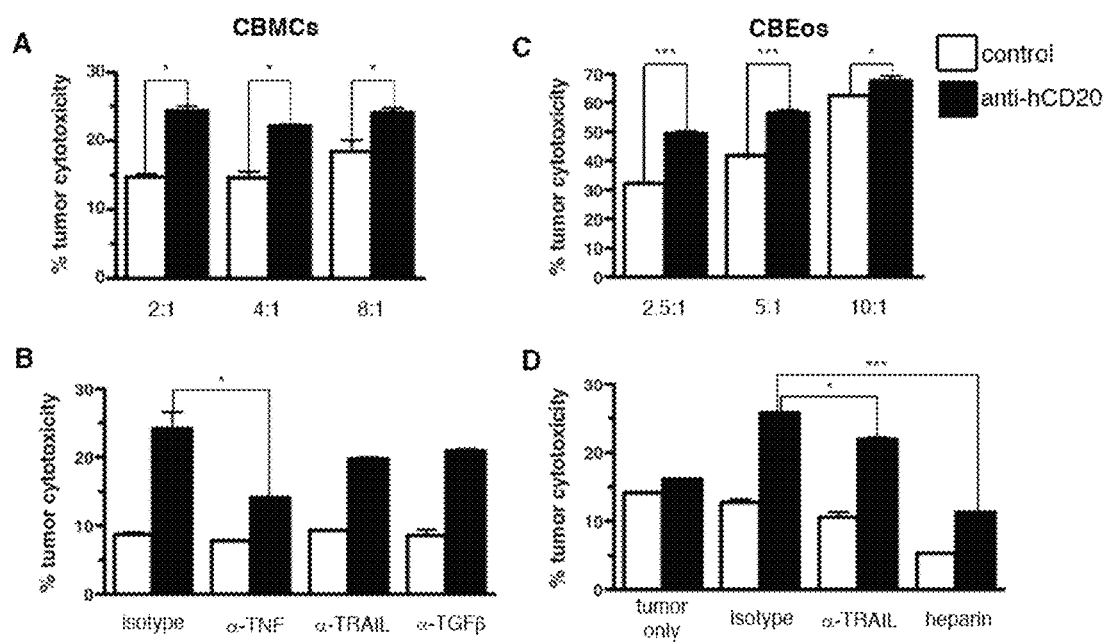
FIG. 2. Mast cell and eosinophil-mediated tumor cytotoxicity in vitro. Histograms show % $PI^+CFSE^+$ tumor cells. OCI-Ly8 human B cell lymphoma cells ($hCD20^+$) were labeled with $10^{-5}$ mM CFSE for 15 mins. $1 \times 10^5$ labeled cells were mixed with unstained CBMCs and 2.5 µg/ml IgE (A and B) or cord blood-derived eosinophils (CBEos) and 5 µg/ml IgE (C and D), then incubated at 37° C. for 24 h. The cell mixture was stained with propidium iodide (PI) before flow cytometric analysis. The percentage of $PI^+$ cells in the $CFSE^{hi}$ fraction represents total tumor cytotoxicity, and results are shown in histogram form. (A) CBMC and hIgE-mediated tumor cytotoxicity at different effector:target ratios. (B) 2 µg/ml blocking antibodies or isotype control were added (E:T ratio 4:1). (C) CBEos and hIgE-mediated tumor cytotoxicity at different effector:target ratios. (D) 2 µg/ml blocking antibodies or 10 U/ml heparin was added. (E:T ratio 2.5:1). Also shown here are data for tumor death induced by antibodies alone (i.e., in the absence of effector cells). Results shown are mean±SD of one representative experiment. Student's t test *, p<0.05; , p<0.01; *, p<0.005.

To test if activated mast cells can directly induce tumor cell death, we prepared purified, cultured mast cells and incubated them with IgE and tumors. Cultured mast cells derived from cord blood (CBMCs) functionally resemble human mast cells that have been freshly-isolated from tissues (Saito et al., 1996 *J Immunol* 157:343-350). CBMCs were mixed with OCI-Ly8 B cells, in the presence of anti-CD20 (1F5.hIgE) or control (SKO-007) IgE. After 24 h, propidium iodide (PI) was added to label dead cells, and the mixture analyzed by flow cytometry. The percentage of CFSE$^+$ cells that were also PI$^+$ indicated the fraction of dead/dying tumor cells present. An increase in tumor cytotoxicity was observed when 1F5.hIgE was added, compared to the control antibody (FIG. 2A). The magnitude of this effect was not augmented by increasing the effector:target ratio above 2:1.

To investigate the mechanism published assay for antibody-dependent cell phagocytosis (Karagiannis 2003 supra), mast cells were labeled with an antibody to c-kit and the percentage of c-kit+/CFSE+ cells measured in the presence of specific or control IgE. We did not observe any significant IgE dependent phagocytic activity by mast by which CBMCs might induce tumor cell death, the cell mixtures were incubated with a series of blocking antibodies, or a rat IgG1 isotype control. The addition of anti-TNF decreased tumor cytotoxicity from 24.2±3.5% to 14.0±0.3% (FIG. 2B). Slight reductions were seen with the other antibodies tested, but these differences were not statistically significant.

Eosinophils and IgE-Mediated Tumor Cytotoxicity

Tumor eosinophilia has been associated with a favorable prognosis, especially in tumors of the gastrointestinal tract (Fernandez-Acenero et al., 2000 *Cancer* 88:1544-1548;

Iwasaki et al., 1986 *Cancer* 58:1321-1327; Pretlow et al., 1983 *Cancer Res* 43:2997-3000).

Previously, Karagiannis et al. have reported that eosinophils isolated from human peripheral blood mediate cytotoxicity when tested with the ovarian cancer cell line IGROV, in an IgE-dependent fashion Karagiannis et al., 2007 *J Immunol* 179:2832-2843). To obtain sufficient numbers of naïve human eosinophils, we differentiated cord blood mononuclear cells in the presence of IL-3 and IL-5. Eosinophils obtained by this protocol exhibit phenotypic and functional similarities to peripheral blood eosinophils (Zardini et al., 1997 *J Immunol Methods* 205:1-9). After 3 weeks, >95% of live cells in cultures resemble mature eosinophils phenotypically (CD66b$^+$, CD16$^-$) as analyzed by flow cytometry. We designated these cells cord blood-derived eosinophils (CBEos). We mixed CBEos with OCI-Ly8 B cells, and added 5.0 µg/ml of either control (SKO) or tumor specific (1F5.hIgE) IgE antibodies. After 24 h at 37° C., PI was added to label dead cells, and the mixture analyzed by flow cytometry (FIG. 2C). As observed with CBMCs, CBEos triggered increased tumor cell death in the presence of tumor-specific IgE compared to control IgE. Interestingly, the antibody-dependence of this effect was less pronounced at higher effector-target ratios, suggesting that higher eosinophil to tumor ratios can lead to cell death in an antibody-independent fashion.

To investigate the mechanism of CBEos-mediated tumor cytotoxicity, we incubated the cultures with a panel of blocking antibodies and inhibitors (FIG. 2D). We observed a modest decrease in tumor death with blocking antibodies to TNF-Related Apoptosis Inducing Ligand (TRAIL), and a more significant effect upon addition of a low concentration of heparin (10 U/ml). Heparin, an anionic molecule, is thought to exert this effect by neutralizing the cationic proteins released by eosinophils (eosinophil cationic protein (ECP), major basic protein (MBP), eosinophil peroxidase (EPO) and eosinophil derived neurotoxin (EDN)) (Swaminathan et al., 2005 *Biochemistry* 44:14152-14158). These cationic proteins have been shown to cause eukaryotic cell death by disrupting negatively charged cell membranes (Carreras et al., 2003 *Biochemistry* 42:6636-6644).

Cytokine Profiling of Activated CBMCs

A large number of genes are up-regulated by activated mast cells upon their activation by IgE and antigen (Sayama et al., 2002 *Immunol* 3:5). To investigate which cytokines/chemokines are produced by mast cells activated by tumor specific IgE, we performed an unbiased screen for cytokines Supernatants from mast cells activated by coculture with IgE and tumor cells were analyzed for 36 cytokines using a multiplexed bead-based assay. CBMCs were activated through FcεRI for 24 hrs at 37° C. by two methods: co-culture with IgE and anti-IgE, or by co-culture of anti-hCD20 IgE with hCD20-expressing tumor cells. A panel of inflammatory, growth and chemotactic factors were assessed. To identify cytokines significantly up-regulated in activated versus resting mast cells, we applied a 2-class Significance Analysis of Microarrays (SAM) algorithm (q<0.05, fold change>5.0). SAM identified inflammatory cytokines such as macrophage inflammatory protein (MIP)-1α, MIP-1β, granulocyte macrophage colony stimulating factor (GM-CSF), epithelial neutrophil activating peptide 78 (ENA78) and IL-8. As expected, the strength of the response was greater when mast cells were activated with a multi-valent antigen (e.g. a cell surface antigen), than when activated by simple bivalent crosslinking (IgE+anti-IgE).

Example 3

Anti-MUC1 IgE Antibodies Inhibit In Vivo Tumor Growth

To test the in vivo anti-tumor activity of anti-hMUC1 IgE (3C6.hIgE), we created a murine cell line that expressed the transmembrane form of hMUC1. We transfected the full-length hMUC1 cDNA into the murine breast carcinoma 4T1. 4T1 was isolated from a spontaneously arising mammary carcinoma in a Balb/c mouse (Dexter et al., 1978 *Cancer Res* 38:3174-3181) and has been used as a transplantable model of breast cancer (Pulaski et al., 2001 *Curr Protoc Immunol* Chapter 20:Unit 20 22). 4T1.hMUC1 expresses abundant hMUC1 on its cell surface, and grows subcutaneously in hFcεRI transgenic mice with kinetics similar to those observed for the parental 4T1 cell line.

Human FcεRI Mouse Model

To study the in vivo effects of targeting tumors with chimeric human IgE antibodies, we used a human FcεRIα transgenic mouse (hFcεRI Tg$^+$). In these mice, the endogenous gene encoding the α-subunit of the high affinity IgE receptor, FcεRIα, has been disrupted, and the mice are transgenic for the human homologue, under the control of the human FcεRIα promoter (Dombrowicz et al., 1996 *J Immunol* 157:1645-1651). In contrast to wild type mice, where FcεRIα expression is limited to mast cells and basophils, the range of expression of FcεRIα in hFcεRI Tg$^+$ mice resembles that seen in humans. In addition to mast cells and basophils, in hFcεRI Tg$^+$ mice (and humans) FcεRI is expressed on eosinophils, monocytes, Langerhans cells, B cells and eosinophils (Kinet, J. P. 1999 *Annu Rev Immunol* 17:931-972; Kayaba et al., 2001 *J Immunol* 167:995-1003). The hFcεRIα gene product has the capacity to complex with the mouse beta and gamma subunits to form a functional 4 chain receptor ($\alpha\beta\gamma_2$). hFcεRI Tg$^+$ mice mount an anaphylactic response to human IgE antibodies and allergen (Dombrowicz et al., 1996 supra).

To verify the ability of these mice to respond to human IgE, we administered 4T1.hMUC1 tumor cells into the peritoneum, followed by either control IgE (derived from SKO-007) or anti-hMUC1 human IgE (3C6.hIgE) on day 9. After 24 h, peritoneal lavage was performed, the cells collected, cytospins made, and stained with hematoxylin, eosin and toluidine blue. Mast cells from the control group were intact, while those from the anti-hMUC1 group showed clear evidence of degranulation. This indicates that mast cells from hFcεRI Tg$^+$ mice are able to respond to human IgE in an antigen-specific manner.

Tumor-Specific IgE Inhibits In Vivo Tumor Growth

The capacity of hMUC1-specific IgE to affect 4T1.hMUC1 tumor growth in vivo was tested in hFcεRI Tg$^+$ mice. For these experiments, we considered the intravenous and intraperitoneal delivery of IgE. We found that IgE is rapidly cleared in vivo. This observation along with the fact that subcutaneous tumors are not well vascularized, led us to administer the drug in the peritumoral region.

Figure 3:
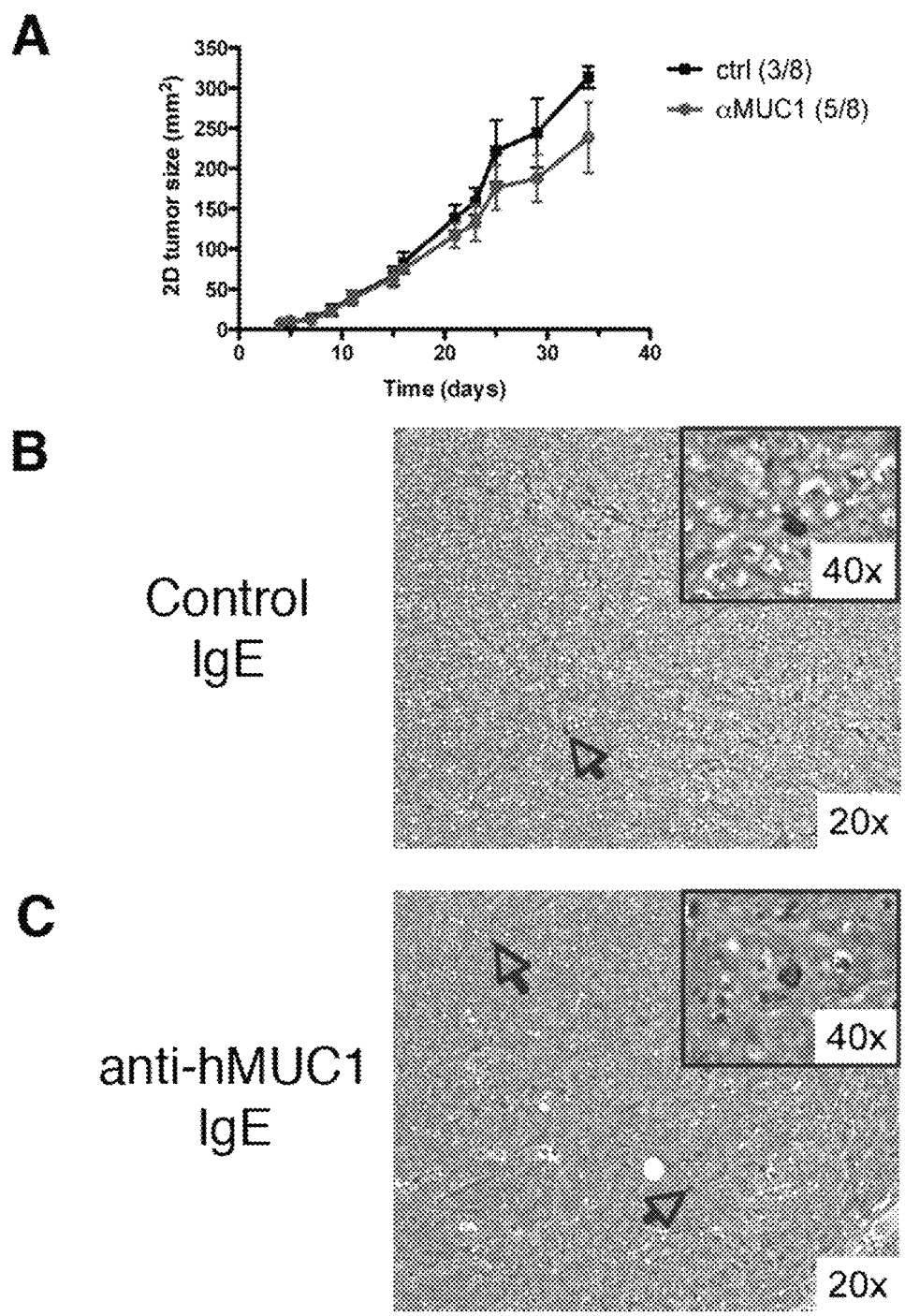
FIG. 3. Tumor-specific IgE inhibits tumor growth in vivo. $10^5$ 4T1.hMUC1 tumor cells were inoculated s.c. into the flanks of hFcεRI mice at d0. 20 µg control or 3C6.hIgE (anti-hMUC1) was administered at d1, 2, 3, 4, and 5. 2-dimensional caliper measurements were taken until tumors exceeded 300 $mm^2$ in area. (A) Graph of average tumor size against time. Error bars represent mean±SD of each group. Number of surviving/total mice per group at the last time point is indicated in brackets. The anti-hMUC1 group is significantly different from the control group (2 way ANOVA, p<0.001). (B and C) Tumors were harvested from surviving mice at d34 from the experiment shown in (A), sectioned, and stained for mast cells. Mast cells were mostly absent in the core of the tumors and in peri-tumor regions. Mast cells that were present (red arrows) were not degranulated (B). Only one tumor from a mouse in the 3C6.hIgE treatment group contained a region that was infiltrated with mast cells, which showed evidence of degranulation (C).

4T1.hMUC1 tumor cells (a total of $10^5$) were inoculated subcutaneously (s.c.) into the shaved flanks of mice, and treated with 20 µg SKO or 3C6.hIgE on days 1, 2, 3, 4 and 5 (FIG. 3A). We observed a modest inhibition of tumor growth in mice treated with 3C6.hIgE (24% reduction in tumor size, p<0.001 by two-way ANOVA). Also, only 3 of 8 mice in the control group survived to day 34, while 5 of 8 mice in the anti-hMUC1 group were still alive.

Tumor samples were obtained from surviving mice at day 34, and stained for the presence of mast cells using toluidine blue (FIG. 3C). We detected the presence of peri- and intra-tumoral mast cells in tumors from mice treated with control IgE. No significant increase in mast cell or inflammatory cell numbers was observed in the 3C6.hIgE treated mice, except for one mouse, which had mast cell infiltration of one tumor section, accompanied by evidence of mast cell degranulation. Tumors retained hMUC1 expression even after treatment with anti-hMUC1 IgE (3C6.hIgE), as analyzed by immunohistochemistry.

Enhanced Tumor Responses with Local Delivery of Tumor-Specific IgE and Chemokines.

The absence of pronounced anti-tumor responses in our in vivo model may be due two factors: first, the inability to deliver adequate amounts of antibody to a poorly vascularized and rapidly growing subcutaneous tumor; and second, the lack of sufficient effector cells in the microenvironment of these transplanted tumors. To test these variables, we created 4T1 cell lines that produced anti-hMUC1 mouse IgE (mIgE) or chemoattractant cytokines MCP-1 and IL5 (Table 1).

TABLE 1

4T1 derivative cell lines

|  | 4T1/ 3C6.mIgE | 4T1.hMUC1/ IL-5 | 4T1.hMUC1/ MCP-1 |
|---|---|---|---|
| Cell surface hMUC1 expression | − | + | + |
| Anti-hMUC1 mouse IgE production | 1 ug/ml[a] | − | − |
| Mouse IL-5 production | − | 10 ng/ml[b] | − |
| Mouse MCP-1 production | − | − | 1 ng/ml[b] |

[a] measured in a mouse IgE specific ELISA assay
[b] measured at confluence in a mouse cytokine specific capture ELISA assay We chose MCP-1/CCL2 because of reports that this cytokine is produced by tumor cells in response to oncogene activation and may be responsible for chemotaxis of monocytes and mast cells into the peritumoral stroma (Soucek et al., 2007 *Nat Med* 13:1211-1218). Interleukin is both a growth factor and chemotactic factor for eosinophils (Sanderson, C. J. 1988 *Dev Biol Stand* 69:23-29). We mixed combinations of the antigen/cytokine producing 4T1 cells with mIgE producing 4T1 cells and injected them subcutaneously in hFcεRI Tg+ mice (FIG. 4A). Mixtures of antibody producing and antigen expressing tumors grew progressively as did tumors that expressed both MCP-1 and IL-5 but lacked local antibody production. In contrast, tumors that expressed anti-hMUC1 mouse IgE, the target antigen, and both cytokines failed to grow in 7 of 8 mice (FIG. 4B). In the single mouse that developed a tumor, it was only visible beginning on day 19 instead of day 8. Eosinophil-containing immune infiltrates were observed in tumors expressing MCP-1 and IL5. However, tumor elimination was only observed when tumor-specific IgE was also present. These data suggest that when sufficient amounts of tumor specific IgE is delivered to an antigen-bearing tumor, in the presence of allergic effector cells, a complete and durable response can be observed.

Interestingly, when wild type 4T1 tumor cells (producing neither hIgE nor chemokines) were injected s.c. into the opposite flank of the 7 mice which had rejected their tumors, the wild type tumors failed to develop after 30 days (data not shown). These data suggest that IgE+chemokine transfected tumor cells may be used prophylatically as a tumor vaccine.

Figure 5:
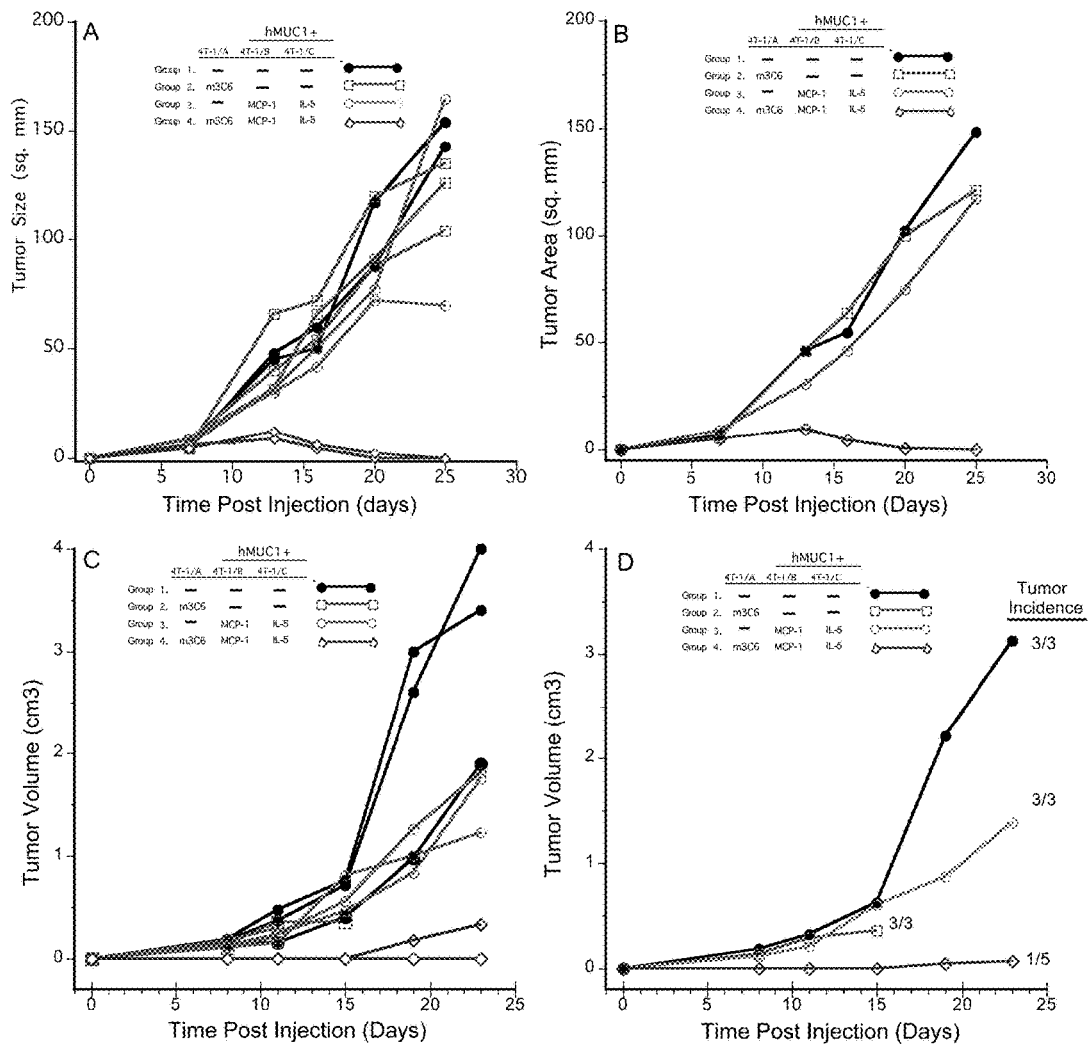
FIG. 5. Mouse IgE specific for hMUC1 mediates complete tumor rejection in FIεRI KO/Tg mice. Individual growth curves and averages of tumor measurements from a repeat experiment of the one shown in FIG. 6. 4T1 tumor cells expressing either 3C6.mIgE or cytokines, were mixed as shown in FIG. 6A. Data are from individual tumor measurements (A,C) or the averages of the tumor volumes (B,D). Note that in the repeat experiment, there was one group 4 tumor that exhibited growth, albeit at greatly reduced growth kinetics.

To confirm this important observation, this experiment was repeated, and the results are shown in FIG. 5 (panel C, individual tumors, and panel D, average of the tumor volumes). In the group 4 mice, one tumor was observed, which grew with greatly reduced kinetics, compared to the other tumor groups. In this repeat experiment, we observed that mice bearing group 3 tumors (antigen+cytokines only) developed overt signs of metastases early in the course of tumor growth. We speculated that the tumors implanted in group 3 grew somewhat slower than groups 1 or 2 because the mice in which they were growing was sick, and lost weight early in the course of the experiment.

Example 4

IgE Antibodies Inhibit Tumor Metastases

Figure 4:
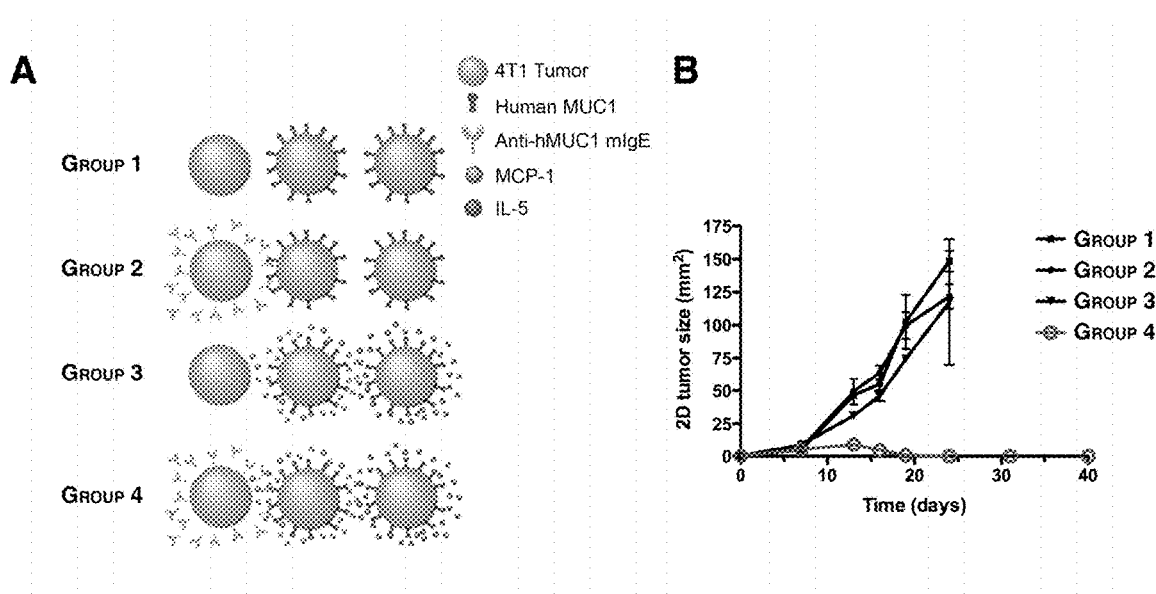
FIG. 4. Mouse IgE specific for hMUC1 mediates complete tumor rejection in FcεRI. Four different combinations of 4T1 tumor cells transfected with human MUC1, anti-hMUC1 IgE (3C6.mIgE) and/or cytokines (MCP-1, IL-5) were inoculated s.c. into the flanks of hFcεRI $Tg^+$ mice at d0. $10^5$ total cells were administered per mouse (n=4 per group). (A) Description of the four experimental groups. (B) The experiment was designed to test the interaction of the IgE antibody with the cognate antigen (MUC1) and the myeloid cells attracted by two cytokines examined. The cells were mixed immediately before injection and then injected subcutaneously into the flanks of FcεRI KO/Tg mice (100,000 cells/mouse). Tumor growth was monitored by two dimensional caliper growth. Progressive growth was observed in each group, except for group 4, where the tumors were transiently palpable, then permanently regressed. Data shown is representative of two separate experiments. Error bars represent average tumor size±SD.

The experiment described in FIG. 4 of Example 3 was repeated with wild-type mice (Balb/c) instead of the human FcεRIα transgenic mice described in Example 3. This was done to assess the contribution of the spectrum of expression of FcεRI in the transgenic mice, compared to the wild type mice, in mediating the observed tumor response.

Figure 6:
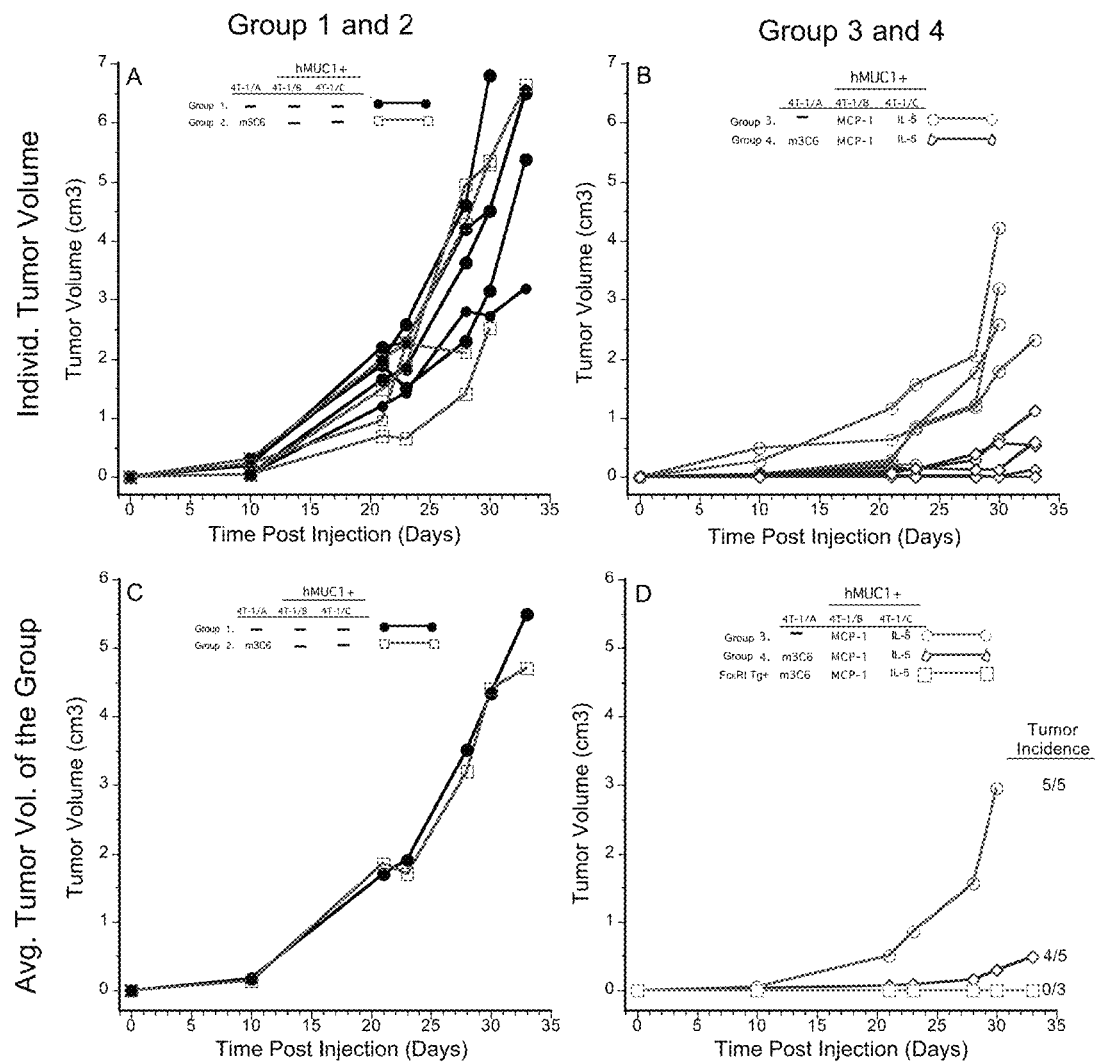
FIG. 6. Mouse IgE specific for hMUC1 is unable to mediate complete tumor rejection in wild type mice, but reveals the ability to prevent metastases. Groups of 4T1 tumor cells expressing either 3C6.hIgE or cytokines were mixed as shown in FIG. 6A, and injected into Balb/c mice. Shown are the individual tumor growth curves (A,B), and averages of the group (C,D). Group 4 tumors, which did not grow in the FcεRI KO/Tg mice, grew in the wild type mice, although with greatly reduced growth kinetics. Note that the group 3 tumors (4T1/hMUC1 and cytokines alone) exhibited intermediate growth kinetics. Three FcεRI KO/Tg transgenic mice were included in this experiment as a positive control, and all three failed to demonstrate any tumor growth when injected with group 4 tumors (panel D, □—□). The reduced growth kinetics of the group 3 tumors (MUC1 and cytokines only) is likely from the fact that these mice develop metastases early in the course of tumor development, and begin to lose weight by day 10 (FIG. 7). The mice bearing group 4 tumors (3C6-mIgE+MUC1+cytokines), demonstrate no weight loss, or other overt signs of metastases, despite having small tumors in their flanks.
Figure 7:
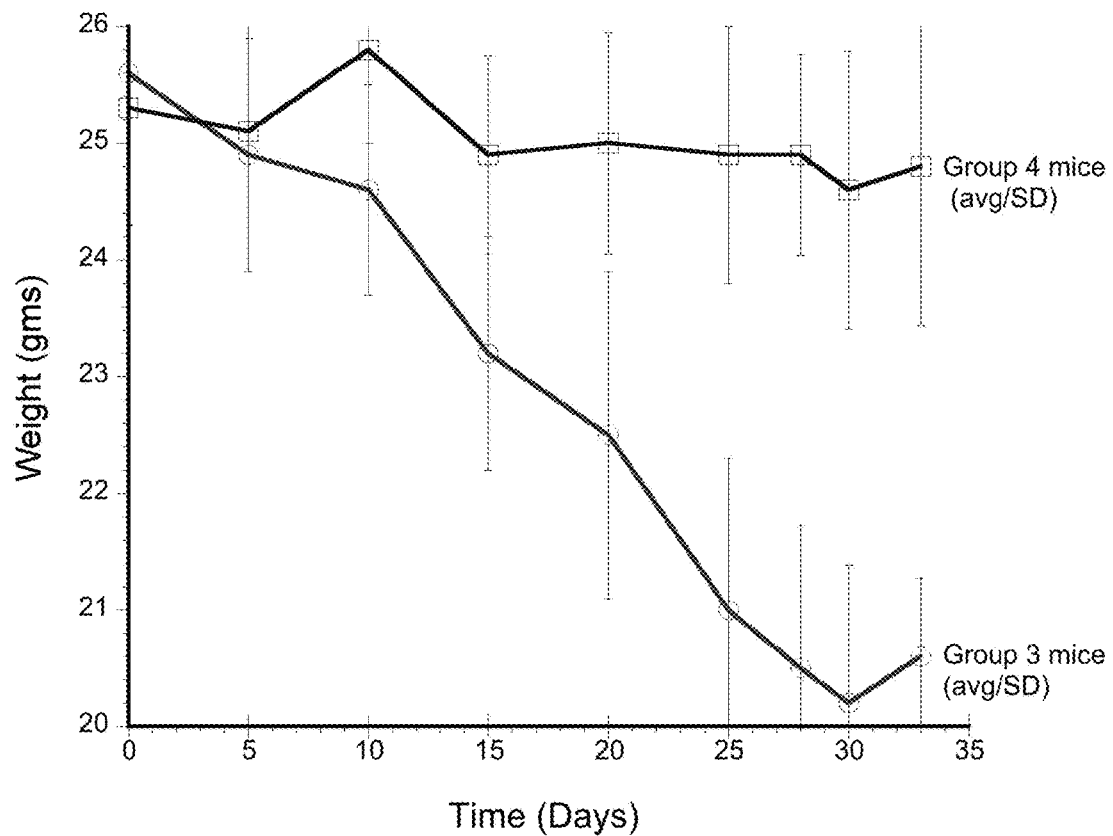
FIG. 7. Weight loss kinetics in groups 3 and 4 mice. Wild-Type mice injected with groups 3 and 4 tumors were weighed every 5 days and the average and standard deviations were calculated. Note that significant differences in average weight between the two groups were detectable by day 10. Mice in group 3 rapidly lost weight, developed ascites, and got ruffled fur. None of these signs of systemic metastases developed in wild type mice bearing group 4 tumors.

When the experiment described in example 3 was repeated in wild type mice, we observed a different result. Instead of complete tumor rejection of the Group 4 tumors, as had been seen in the transgenic mice (FIGS. 4B and 5), very small tumors, with greatly reduced growth kinetics, emerged in Group 4 wild-type mice (FIG. 6). Three FcεRIα transgenic mice were included in this experiment as a positive control. None of three (0/3) Tg+ mice with implanted group 4 tumors showed tumor growth (FIG. 6D, □—□).

Even though the Group 4 tumors in wild-type mice grew with greatly reduced kinetics, they still grew progressively. As we had observed in the previous experiment with Tg+ mice, the group 3 tumors in wild-type mice developed metastases very early in the course of the experiment. The Group 3 wild-type mice lost weight, developed ascites, and got ruffly fur. However, in the Group 4 wild-type mice, even though they developed small tumors that lagged in growth and appearance from Groups 1, 2 and 3, the mice did not develop signs of metastatic disease as seen in mice with group 3 tumors. That is, even though the tumors were present under the skin in all of the mice, the effect of the cytokines MCP-1/IL-5 on tumor behavior (metastases) was completely reversed under the influence of 3C6-mIgE. The mice with group 4 tumors were followed for a month, and the mice never developed overt metastases though they had very slowly progressively growing tumors on their flanks. The results of this key experiment are summarized in Table 2 below.

TABLE 2

| Tumor Group | Tumor growth Fc-Epsilon transgenic | Metastasis Fc-Epsilon transgenic | Tumor Growth Wild type | Metastasis Wild type |
|---|---|---|---|---|
| Group 1: MUC1 | +++++ | ----- | +++++ | ------ |
| Group 2: MUC1 plus MUC1 IgE | +++++ | ----- | +++++ | ------- |
| Group 3: MUC1, IL-5 plus MCP-1 | +++ | ++ | +++ | +++++ |

TABLE 2-continued

| Tumor Group | Tumor growth Fc-Epsilon transgenic | Metastasis Fc-Epsilon transgenic | Tumor Growth Wild type | Metastasis Wild type |
|---|---|---|---|---|
| Group 4: MUC1, 3C6-mIgE, IL5, and MCP1 | ----- | ---- | + | ------ |

MUC1 = 4T-1/MUC1; MUC1 IgE = 4T-1 transfected with the 3C6 mouse heavy and light chain specific for hMUC1; IL5 = 4T1/hMUC1 transfected with the cDNA for mIL5); MCP-1 = 4T1/hMUC1 transfected with the cDNA for MCP-1.

Early metastases was seen in experiments done in both the Tg+ and wild type mice bearing group 3 tumors. This was completely reversed in mice bearing group 4 tumors. The difference between the Tg+ and wild type mice, was that in the Tg+ mice, the mice injected with group 4 tumors, never develop palpable tumors. In the wild type mice, the group 4 tumors grow, albeit, slowly. Therefore, the effect on the mIgE antibody has to be on reprogramming the cells drawn to the tumor by the cytokines, and not strictly inhibition of tumor growth, per se. A reasonable explanation of why the mice with group 4 tumor in Tg+ mice do not develop metastases is that the tumor is eliminated at the site of injection by an allergic immune response. However, in the wild type mice, the metastatic phenotype is eliminated, by mIgE, independent of the presence of the tumor. In other words, only when the experiment is conducted in wild type mice, could we observe that the effect of the cytokines on the tumor was reversible (FIG. 6), and that the 3C6-mIgE antibody was able to reprogram the myeloid cells in and around the tumor, likely by preventing tumor engraftment (in the Tg+ mice), or greatly slowing their growth (WT mice), but in both cases, preventing tumor metastases.

In addition, the experiment conducted with wild-type mice also shows that the antibody can control an established tumor, as their growth kinetics in the wild type mice are dramatically reduced (FIG. 6).

Therefore, one feature of the IgE antibodies of the invention is their ability to prevent circulating cells from setting up required microenvironments in the liver, lungs and bones that are necessary prior to the appearance of overt metastases from a primary tumor. IgE antibodies, unlike IgG antibodies, migrate out of the vascular space to every tissue in the body. Thus IgE antibodies would be uniquely position to prevent circulating cells from forming a microenvironment necessary to support metastases. Treatment with such IgE antibodies would therefore prevent metastases and recurrence of cancer.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It will also be understood that none of the embodiments described herein are mutually exclusive and may be combined in various ways without departing from the scope of the invention encompassed by the appended claims.

What is claimed is:

1. An IgE monoclonal antibody that specifically binds an epitope of MUC1 and is capable of modulating immune effector cells to inhibit tumor metastasis having a heavy chain variable region encoded by a nucleic acid comprising CDRs 1-3 of a heavy chain variable region encoded by SEQ ID NO: 1 and a light chain variable region encoded by a nucleic acid comprising CDRs 1-3 of a light chain variable region encoded by SEQ ID NO: 2, optionally humanized.

2. The antibody of claim 1, which has a constant region that is of human origin.

3. The antibody of claim 1, which is a chimeric antibody.

4. The antibody of claim 1, which is a humanized antibody.

5. The antibody of claim 1, which is 3C6.hIgE.

6. A method for inhibiting metastasis of a solid tumor in a patient, comprising the step of administering to the patient the antibody of claim 1.

7. The method of claim 6, wherein the antibody has a constant region that is of human origin.

8. The method of claim 6, wherein the antibody is a chimeric antibody.

9. The method of claim 6, wherein the antibody is a humanized antibody.

10. The method of claim 6, wherein the antibody is 3C6.hIgE.

11. The method of claim 6, wherein the antibody is administered to the patient prior to the development of metastasis in the patient.

12. The method of claim 6, wherein the solid tumor is of epithelial origin.

13. The method of claim 6, wherein the solid tumor is breast cancer, colorectal cancer, ovarian cancer, renal cancer, prostate cancer, bladder cancer, gastrointestinal cancer, pancreatic cancer, or lung cancer.

* * * * *